(12) United States Patent
Maynard et al.

(10) Patent No.: US 6,852,730 B2
(45) Date of Patent: Feb. 8, 2005

(54) SUBSTITUTED FUSED PYRAZOLECARBOXYLIC ACID ARYLAMIDES AND RELATED COMPOUNDS

(75) Inventors: George Maynard, Clinton, CT (US); Jun Yuan, Guilford, CT (US); Stanislaw Rachwal, Branford, CT (US)

(73) Assignee: Neurogen Corporation, Branford, CT (US)

( * ) Notice: Subject to any disclaimer, the term of this patent is extended or adjusted under 35 U.S.C. 154(b) by 36 days.

(21) Appl. No.: 10/360,963

(22) Filed: Feb. 7, 2003

(65) Prior Publication Data

US 2003/0216379 A1 Nov. 20, 2003

Related U.S. Application Data

(60) Provisional application No. 60/355,314, filed on Feb. 7, 2002.

(51) Int. Cl.[7] ............... A61K 31/437; A61K 31/55; A61K 31/519; C07D 471/04; C07D 487/14
(52) U.S. Cl. ............... 514/293; 514/215; 514/267; 540/579; 544/251; 546/82
(58) Field of Search .................. 546/82; 514/293, 514/215, 267; 544/251; 540/579

(56) References Cited

U.S. PATENT DOCUMENTS

| | | |
|---|---|---|
| 5,484,944 A | 1/1996 | Albaugh et al. |
| 5,608,079 A | 3/1997 | Albaugh et al. |
| 5,723,462 A | 3/1998 | Albaugh et al. |
| 5,750,702 A | 5/1998 | Albaugh et al. |
| 5,804,686 A | 9/1998 | Albaugh et al. |
| 5,925,770 A | 7/1999 | Albaugh et al. |
| 6,080,873 A | 6/2000 | Albaugh et al. |
| 6,096,887 A | 8/2000 | Albaugh et al. |
| 6,211,365 B1 | 4/2001 | Albaugh et al. |
| 6,353,109 B1 | 3/2002 | Albaugh et al. |
| 6,395,905 B1 | 5/2002 | Bryant et al. |

FOREIGN PATENT DOCUMENTS

| | | |
|---|---|---|
| GB | 2 352 630 A | 2/2001 |
| GB | 2 352 632 A | 2/2001 |
| WO | WO 99/25684 | 5/1999 |
| WO | WO 01/16103 A1 | 3/2001 |
| WO | WO 01/44244 * | 6/2001 |
| WO | WO 02/12442 A2 | 2/2002 |
| WO | WO 02/20480 A1 | 3/2002 |
| WO | WO 02/20492 A1 | 3/2002 |
| WO | WO 02/46155 A1 | 6/2002 |
| WO | WO 03/004018 A1 | 1/2003 |

* cited by examiner

*Primary Examiner*—Evelyn Mei Huang
(74) *Attorney, Agent, or Firm*—McDonnell Boehnen Hulbert & Berghoff LLP

(57) ABSTRACT

Heterocyclic compounds such as 3,4,5,6-tetrahydro-2,3,10-triaza-benzo[e]azulene-1-carboxylic acid arylamides, 5,7-Dihydro-6H-pyrazolo[3,4-h]quinoline-9-carboxylic acid arylamides, 5,7-Dihydro-6H-pyrazolo[3,4-h]quinazoline-9-carboxylic acid arylamides, 2,4,5,6-Tetrahydro-1,2,6,7-tetraaza-as-indacene-8-carboxylic acid arylamides and related compounds are disclosed. These compounds are highly selective agonists, antagonists or inverse agonists for $GABA_A$ brain receptors or prodrugs of agonists, antagonists or inverse agonists for $GABA_A$ brain receptors and are therefore useful in the treatment of anxiety, depression, sleep and seizure disorders, overdose with benzodiazepine drugs, Alzheimer's dementia, and for enhancement of memory. Pharmaceutical compositions, including packaged pharmaceutical compositions, are further provided. Intermediates useful for the synthesis of pyrazolecarboxylic acid arylamides are also provided. Compounds of the invention are also useful as probes for the localization of $GABA_A$ receptors in tissue samples.

19 Claims, No Drawings

SUBSTITUTED FUSED PYRAZOLECARBOXYLIC ACID ARYLAMIDES AND RELATED COMPOUNDS

CROSS REFERENCE TO RELATED APPLICATIONS

This application claims priority from U.S. Provisional Application Ser. No. 60/355,314, filed Feb. 7, 2002, the disclosure of which is incorporated herein by reference in its entirety.

FIELD OF THE INVENTION

This invention relates to substituted fused pyrazolecarboxylic acid arylamides and related compounds, such as substituted fused pyrazolecarboxylic acid arylamides that bind with high selectivity and high affinity to the benzodiazepine site of $GABA_A$ receptors. This invention also relates to pharmaceutical compositions comprising such compounds and to the use of such compounds in treatment of central nervous system (CNS) diseases.

BACKGROUND

The $GABA_A$ receptor superfamily represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization.

A number of cDNAs for $GABA_A$ receptor subunits have been characterized. To date at least 6α, 3β, 3γ, 1ε, 1δ and 2ρ subunits have been identified. It is generally accepted that native $GABA_A$ receptors are typically composed of 2α, 2β, and 1γ subunits (Pritchett & Seeburg *Science* 1989; 245:1389–1392 and Knight et al., *Recept. Channels* 1998; 6:1–18). Evidence such as message distribution, genome localization and biochemical study results suggest that the major naturally occurring receptor combinations are $α_2β_2γ_2$, $α_2β_3γ_2$, $α_3β_3γ_2$, and $α_5β_3γ_2$ (Mohler et al., *Neuroch. Res.* 1995; 20(5): 631–636).

Benzodiazepines exert their pharmacological actions by interacting with the benzodiazepine binding sites associated with the $GABA_A$ receptor. In addition to the benzodiazepine site, the $GABA_A$ receptor contains sites of interaction for several other classes of drugs. These include a steroid binding site, a picrotoxin site, and the barbiturate site. The benzodiazepine site of the $GABA_A$ receptor is a distinct site on the receptor complex that does not overlap with the site of interaction for GABA or for other classes of drugs that bind to the receptor (see, e.g., Cooper, et al., The Biochemical Basis of Neuropharmacology, 6th ed., 1991, pp. 145–148, Oxford University Press, New York). Early electrophysiological studies indicated that a major action of the benzodiazepines was enhancement of GABAergic inhibition. Compounds that selectively bind to the benzodiazepine site and enhance the ability of GABA to open $GABA_A$ receptor channels are agonists of GABA receptors. Other compounds that interact with the same site but negatively modulate the action of GABA are called inverse agonists. Compounds belonging to a third class bind selectively to the benzodiazepine site and yet have little or no effect on GABA activity, but can block the action of $GABA_A$ receptor agonists or inverse agonists that act at this site. These compounds are referred to as antagonists.

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have a long history of pharmaceutical use as anxiolytics, these compounds often exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of other CNS active compounds. For example, there is evidence that selective serotonin reuptake inhibitors (SSRIs) may show greater antidepressant activity when used in combination with $GABA_A$ selective ligands than when used alone.

SUMMARY OF THE INVENTION

This invention provides substituted fused pyrazolecarboxylic acid arylamides that bind, preferably with both high affinity and high selectivity, to the benzodiazepine site of the $GABA_A$ receptor, including human $GABA_A$ receptors.

Thus, the invention provides compounds of Formula I, and pharmaceutical compositions comprising compounds of Formula I.

The invention further comprises methods of treating patients suffering from CNS disorders with an effective amount of a compound of the invention. The patient may be a human or other mammal. Treatment of humans, domesticated companion animals (pets), or livestock animals suffering from CNS disorders with an effective amount of a compound of the invention is encompassed by the invention.

In a separate aspect, the invention provides a method of potentiating the actions of other CNS active compounds. This method comprises administering an effective amount of a compound of the invention with another CNS active compound.

Additionally this invention relates to the use of the compounds of the invention as probes for the localization of $GABA_A$ receptors in tissue sections.

Accordingly, the invention includes compounds of Formula I and the pharmaceutically acceptable salts thereof.

Formula I

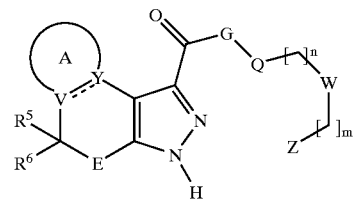

E, in Formula I, represents $(CR^1R^2)_k$, wherein $R^1$ and $R^2$ are independently chosen from hydrogen, halogen, hydroxy, cyano, nitro, amino, alkyl, alkenyl, alkynyl, haloalkyl, haloalkoxy, mono or dialkylamino, and alkoxy, where k is 0, 1, 2, or 3.

G is either oxygen or NH.

The group

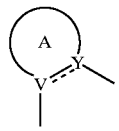

represents an optionally substituted saturated, partially unsaturated, or aromatic heterocyclic ring having from 5 to 7 ring atoms, wherein from 1 to 4 ring atoms are selected from nitrogen, oxygen and sulfur, the remaining ring atoms are carbon, and the V===Y bond is a single, double, or aromatic bond. V is nitrogen, carbon or CH, and Y is carbon or CH.

$R^5$ and $R^6$, in Formula I, may be taken together to form a carbonyl group; or $R^5$ and $R^6$ are independently chosen from hydrogen, halogen, hydroxy, haloalkyl, haloalkoxy, nitro, cyano, —COOH, amino, $R_{10}$, —NH($R_{10}$), —N($R_{10}$)($R_{11}$), —O($R_{10}$), —SO$_2$NH$_2$, —SO$_2$NH($R_{10}$), —SO$_2$N($R_{10}$)($R_{11}$), —NHCO($R_{10}$), —N($R_{10}$)CO($R_{11}$), —NHCO$_2$($R_{10}$), —N($R_{10}$)CO$_2$($R_{11}$), —NHSO$_2$($R_{10}$), —N($R_{10}$)SO$_2$($R_{11}$), —SO$_2$NHCO($R_{10}$), —SO$_2$N($R_{10}$)CO($R_{11}$), —CONHSO$_2$($R_{10}$), —CON($R_{10}$)SO$_2$($R_{11}$), —CONH$_2$, —CONH($R_{10}$), —CON($R_{10}$)($R_{11}$), —CO$_2$($R_{10}$), —CO($R_{10}$), —SO$_{0-2}$($R_{10}$) optionally substituted aryl, and optionally substituted heteroaryl.

$R_{10}$ and $R_{11}$ are independently chosen from straight, branched, and cyclic alkyl groups and (cycloalkyl)alkyl groups, said straight, branched, and cyclic alkyl groups and (cycloalkyl)alkyl groups consisting of 1 to 8 carbon atoms, and containing zero or one or more double or triple bonds, each of which 1 to 8 carbon atoms may be further substituted with one or more substituent(s) independently chosen from hydroxy, oxo, halogen, amino, mono or dialkylamino, cyano, nitro, alkoxy, —COOH, —SO$_2$NH$_2$, —SO$_2$NH(alkyl), —SO$_2$N(alkyl) (alkyl), —NHCO(alkyl), —N(alkyl)CO(alkyl), —NHCO$_2$(alkyl), —N(alkyl)CO$_2$(alkyl), —NHSO$_2$(alkyl), —N(alkyl)SO$_2$(alkyl), —SO$_2$N(alkyl)CO(alkyl), —SO$_2$NHCO(alkyl), —CON(alkyl)SO$_2$(alkyl), —CONHSO$_2$(alkyl), —CONH$_2$, —CONH(alkyl), —CON(alkyl)(alkyl), —CO$_2$(alkyl), —CO(alkyl), —SO$_{0-2}$(alkyl), cycloalkyl, aryl, heteroaryl, and heterocycloalkyl.

Q is an optionally substituted aryl or optionally substituted heteroaryl group.

W is hydrogen, oxygen, NR$^7$, sulfur, or CR$^7$R$^8$ where R$^7$ and R$^8$ are the same or different and represent hydrogen, straight or branched chain alkyl, or CR$^7$R$^8$ represents a cycloalkyl group having from 3 to 7 carbon atoms. When W is hydrogen, m is 0 and Z is absent.

Z is absent, hydrogen, hydroxy, straight or branched chain alkoxy, cycloalkyl, cycloalkyl(alkoxy), amino, mono or dialkylamino, or NR$_{12}$COR$_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group.

The groups

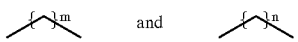

represent methylene groups which may be substituted with halogen, cyano, nitro, amino, mono or dialkylamino, alkenyl, alkynyl, alkoxy, trifluoromethyl, trifluoromethoxy, straight or branched chain alkyl, or cycloalkyl; m is 0, 1, 2, or 3; and n is 0, 1, 2, or 3.

The invention further provides intermediates of Formula VIII (shown below) useful in the synthesis of compounds of Formula I.

DETAILED DESCRIPTION OF THE INVENTION

Prior to setting forth the invention in detail, it may be helpful to provide definitions of certain terms to be used herein. Compounds of the present invention are generally described using standard nomenclature. Certain compounds are described herein using a general formula that includes variables. Unless otherwise specified, each variable within such a formula is defined independently of other variables.

The compounds herein described may have one or more asymmetric centers. Compounds of the present invention containing an asymmetrically substituted atom may be isolated in enantiomerically enriched or racemic form. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent; derivatizing with an enantiomerically enriched resolving reagent, separating the resulting diastereomers through means well known in the art, and removing the enantiomerically enriched resolving reagent through ordinary chemical means such as, for example, hydrolysis or hydrogenation; or chromatography, using, for example a chiral HPLC column.

Many geometric isomers of olefins, carbon-nitrogen double bonds, and the like can also be present in the compounds described herein, and all such stable isomers are contemplated in the present invention. Cis and trans geometric isomers, as well as E and Z isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

Some compounds of the invention may exist as tautomers. Unless otherwise specified, any description or claim of one tautomeric form is intended to encompass the other tautomer.

The term "substituted", as used herein, means that any one or more hydrogens on the designated atom is replaced with a selection from the indicated group, provided that the designated atom's normal valence is not exceeded, and that the substitution results in a stable compound. When a substituent is keto (i.e., =O), then 2 hydrogens on the atom are replaced. Groups that are "optionally substituted" may be either unsubstituted or substituted with one or more suitable groups.

Suitable groups or "substituted" moieties of compounds of the invention include e.g., halogen such as fluoro, chloro, bromo or iodo; cyano; hydroxyl; nitro; azido; amino; oxo; alkanoyl such as a $C_1$–$C_6$ alkanoyl group such as acyl and the like; carboxamido; alkylcarboxamido groups; alkyl groups including those groups having 1 to about 8 carbon atoms, or 1, 2, 3, 4, 5, or 6 carbon atoms; alkenyl and alkynyl groups including groups having one or more unsaturated linkages and from 2 to about 8 carbon, or 2, 3, 4, 5 or 6 carbon atoms; alkoxy groups having those having one or more oxygen linkages and from 1 to about 8 carbon atoms, or 1, 2, 3, 4, 5 or 6 carbon atoms; aryloxy such as phenoxy; alkylthio groups including those moieties having one or more thioether linkages and from 1 to about 8 carbon atoms, or 1, 2, 3, 4, 5 or 6 carbon atoms; alkylsulfinyl groups including those moieties having one or more sulfinyl linkages and from 1 to about 8 carbon atoms, or 1, 2, 3, 4, 5, or 6 carbon atoms; alkylsulfonyl groups including those moieties having one or more sulfonyl linkages and from 1 to about 8 carbon atoms, or 1, 2, 3, 4, 5, or 6 carbon atoms; aminoalkyl groups such as groups having one or more N atoms and from 1 to about 8 carbon atoms, or 1, 2, 3, 4, 5 or 6 carbon atoms; mono- and di-alkylamino groups; haloalkyl groups; haloalkoxy groups; alkanoyloxy groups; alkoxycarbonyl groups; carbocyclic groups including carbocyclic aryl having 6 or more carbons, e.g. phenyl and naphthyl, cycloalkyl groups, e.g. cyclopropyl and cyclopropyl(methyl) groups, and partially unsaturated carbocyclic groups, e.g. cyclohexenyl; carbocyclic alkyl groups, e.g. arylalkyl having 1 to 3 separate or fused rings and from 6 to about 18 carbon ring atoms, e.g. benzyl, and cycloalkyl(alkyl) groups, e.g. cyclopropyl(methyl); arylalkoxy having 1 to 3 separate or fused rings and from 6 to about 18 carbon ring atoms; heterocyclic groups, including partially unsaturated, heteroaromatic, and heteroalicyclic groups having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl; and heterocyclic alkyl groups, including heteroaromatic alkyl groups, e.g. pyridylmethyl, and heteroalicyclic alkyl groups.

A dash ("—") that is not between two letters or symbols is used to indicate a point of attachment for a substituent. For example, —CONH$_2$ is attached through the carbon atom.

The invention includes all isotopes of atoms occurring in the compounds. Isotopes include those atoms having the same atomic number but different mass numbers. By way of general example and without limitation, isotopes of hydrogen include tritium and deuterium. Isotopes of carbon include $^{11}C$, $^{13}C$, and $^{14}C$.

When any variable occurs more than one time in any constituent or formula for a compound, its definition at each occurrence is independent of its definition at every other occurrence. Thus, for example, if a group is shown to be substituted with 0–2 R*, then said group may optionally be substituted with up to two R* groups and each R* is selected independently from the definition of R*. Also, combinations of substituents and/or variables are permissible only if such combinations result in stable compounds. Also, for example, dialkylamino groups are understood to contain two alkyl, preferably $C_1$–$C_6$ alkyl, groups that may be the same or different. Thus, dialkylamino encompasses N-ethyl-N-methylamino, N,N-diethylamino, N,N-dimethylamino, N-methyl-N-propylamino, and the like.

Where the term "alkyl" is used, either alone or within other terms such as "haloalkyl" and "aminoalkyl", it embraces linear and branched radicals having one to about eight carbon atoms. More preferred are lower alkyl radicals having one to about six carbon atoms. Examples of alkyl include, but are not limited to, methyl, ethyl, n-propyl, iso-propyl, n-butyl, sec-butyl, tert-butyl, n-pentyl, and sec-pentyl and the like. The term $C_1$–$C_6$ alkyl as used herein includes alkyl groups having from 1 to 6 carbon atoms. Preferred examples are methyl and ethyl. When $C_1$–$C_n$alkyl is used herein in conjunction with another group, for example, ($C_3$–$C_7$cycloalkyl)$C_1$–$C_4$alkyl, the indicated group, in this case cycloalkyl, is by an alkyl chain having the specified number of carbon atoms, in this case from 1 to 4 carbon atoms.

"Alkenyl" is intended to include hydrocarbon chains of either a straight or branched configuration comprising one or more unsaturated carbon-carbon bonds, which may occur in any stable point along the chain, such as ethenyl and propenyl.

"Alkynyl" is intended to include hydrocarbon chains of either a straight or branched configuration comprising one or more triple carbon-carbon bonds that may occur in any stable point along the chain, such as ethynyl and propynyl.

The terms "mono- and di-alkylamino" denote amino groups which have been substituted with one alkyl radical and with two independently selected alkyl radicals, respectively. More preferred alkylamino radicals are alkylamino radicals having one or two independently selected alkyl radicals of one to six carbon atoms each, attached to a nitrogen atom. Suitable "alkylamino" may be mono or dialkylamino such as methylamino, ethylaminodimethylamino, diethylamino or the like.

"Alkoxy" represents an alkyl group as defined above attached to the parent molecular moiety through an oxygen bridge. Examples of alkoxy include, but are not limited to, methoxy, ethoxy, n-propoxy, iso-propoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, and 3-methylpentoxy. More preferred alkoxy groups include methoxy, ethoxy, isopropoxy, and isobutoxy.

The term "aryl" is used to indicate aromatic groups that contain only carbon atoms in the ring structure. Thus, the term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include phenyl, naphthyl, 1,2,3,4-tetrahydronaphthalene, indanyl, and biphenyl. Preferred aryl groups include phenyl, naphthyl, including 1-naphthyl and 2-naphthyl, and acenaphthyl. More preferred aryl groups include phenyl and napthyl. The aryl groups herein are unsubstituted or, as specified, substituted in one or more substitutable positions with various groups. Thus, such aryl groups are optionally substituted with, for example, $C_1$–$C_6$ alkyl, $C_1$–$C_6$ alkoxy, halogen, hydroxy, cyano, nitro, amino, mono- or di-($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino ($C_1$–$C_6$)alkyl, mono- or di($C_1$–$C_6$)alkylamino($C_1$–$C_6$) alkyl.

The term "cycloalkyl" embraces radicals having three to ten carbon atoms. More preferred cycloalkyl radicals are cycloalkyl radicals having three to seven carbon atoms, i.e., $C_3$–$C_7$ cycloalkyl. Examples include radicals such as cyclopropyl, cyclobutyl, cyclopentyl, cyclohexyl and cycloheptyl.

In the term "($C_3$–$C_7$cycloalkyl)alkyl", the $C_3$–$C_7$ cycloalkyl group is attached to the parent molecular moiety through the alkyl, preferably a $C_1$–$C_6$, more preferably a $C_1$–$C_4$ alkyl, group. This term encompasses, but is not limited to, cyclopropylmethyl, and cyclohexylmethyl.

The terms "carbocyclic group" is used herein to indicate saturated, partially unsaturated, or aromatic cyclic groups which typically have from 5 to 8 ring atoms, and more preferably from 5 to 7 ring atoms. In addition to the cycloalkyl and aryl groups described herein, the term "carbocyclic group" encompasses groups such as cyclopentene, cyclohexene, and cyclohexa-1,3-diene.

"Haloalkyl" is intended to include both branched and straight-chain saturated aliphatic hydrocarbon groups having the specified number of carbon atoms, substituted with 1 or more halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge.

The terms "heterocyclic group" or "heterocyclic ring" are used to indicate saturated, partially unsaturated, or aromatic groups, having 1 ring or 2 fused, pendant or spiro rings, 3 to 8 atoms in each ring and in at least one ring between 1 to 3 heteroatoms selected from N, O, or S. The heterocyclic group may be bound through any heteroatom or carbon atom that results in a stable structure. The heterocyclic groups described herein may be substituted on carbon or on a nitrogen atom if the resulting compound is stable. A nitrogen atom in the heterocyclic group may optionally be quaternized. Bicyclic heterocyclic groups may contain 1 ring with is saturated and 1 ring which is partially unsaturated or aromatic, e.g. a tetrahydroquinolinyl group. The term "heterocyclic alkyl group" is used to indicate a heterocyclic group as described attached through an alkyl linker, e.g. a pyridylmethyl group or a morpholinyl ethyl group. The nitrogen and sulfur heteroatoms may optionally be oxidized. The heterocyclic ring may be attached to its pendant group at any heteroatom or carbon atom which results in a stable structure. The heterocyclic rings described herein may be substituted on any substitutable carbon or nitrogen atom that results in a stable compound.

As used herein, the term "heteroaryl" means stable monocyclic, bicyclic and tricyclic ring systems which contain at least one aromatic ring where the aromatic ring contains from 5–7 members and from 1 to 4 hetero atoms independently selected from the group consisting of nitrogen, oxygen, and sulfur; the remaining rings contain from 5–7 members selected from carbon, oxygen, nitrogen, and sulfur. The aromatic ring containing a hetero atom is the "heteroaromatic ring." In bicyclic and tricyclic ring systems, the heteroaromatic ring may be fused to a carbocyclic ring that may be aromatic, such as benzo, or to a heteroaromatic ring, such as pyrido or pyrrolidino, or to heteroaromatic and one carbocyclic ring. Thus, "heteroaryl" includes ring systems having from one to three rings of from 5–7 ring members in each ring and where at least one ring is aromatic and contains from one to four hetero atoms. Any of the rings in the heteroaryl groups may be further fused to another ring forming a spiro ring system.

Examples of heteroaryl groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazblyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, quinazolinyl, quinolinyl, 4H-quinolizinyl, quinoxalinyl, quinuclidinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred heteroaryl groups include, but are not limited to, pyrrolyl, pyrazolyl, imidazolyl, pyridinyl, pyrimidinyl, furanyl, and thienyl groups.

As used herein, the term "heterocycloalkyl" is intended to mean a stable 5-to 7-membered monocyclic or 7-to 10-membered bicyclic ring system which contains at least one non-aromatic ring wherein said ring consists of carbon atoms and from 1 to 4 heteroatoms independently selected from the group consisting of N, O and S. The heterocycloalkyl ring or heterocycloalkyl bicyclic ring system may be fused to a benzene ring. A nitrogen in the heterocycle may optionally be quaternized. It is preferred that when the total number of S and O atoms in the heterocycloalkyl group exceeds 1, then these heteroatoms are not adjacent to one another. It is also preferred that the total number of S and O atoms in the heterocycloalkyl is not more than 1. Examples of heterocycloalkyl groups include but are not limited to tetrahydroquinolinyl, tetrahydroisoquinolinyl, pyrrolyl, piperazinyl, piperidinyl, tetrahydrofuranyl, morpholinyl, azetidinyl, 2H-pyrrolyl.

The term "halogen" indicates fluorine, chlorine, bromine, and iodine.

In a specific aspect, the invention provides compounds of Formula I where A is a pyridyl ring. In another embodiment, the invention provides compounds of Formula I where A is a pyrimidine ring. In a further embodiment, the invention provides compounds of Formula I where A is a pyrazole ring.

In addition to compounds of Formula I

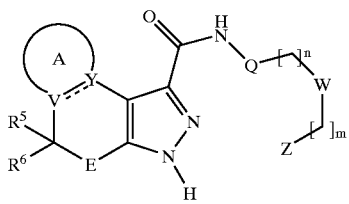

Formula I the invention also provides compounds of the same chemical formula in which the variables carry the definitions set forth below.

E, in this embodiment, represents $(CR^1R^2)_k$, wherein $R^1$ and $R^2$ are independently chosen from hydrogen, halogen, hydroxy, cyano, nitro, amino, $(C_1-C_6)$alkyl, $(C_2-C_6)$alkenyl, $(C_2-C_6)$alkynyl, halo$(C_1C_6)$alkyl, halo$(C_1-C_6)$alkoxy, mono- and di-alkyl$(C_1-C_6)$amino, and $(C_1-C_6)$alkoxy; and k is 0, 1, 2, or 3.

The group

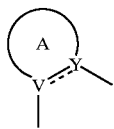

is a group of the formula:

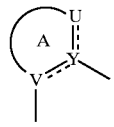

which represents a saturated, partially unsaturated, or aromatic heterocyclic ring selected from thienyl, thiazolyl, pyridyl, pyrimidinyl, imidazolyl, pyrazolyl, pyrazinyl, pyridizinyl, piperidinyl, oxazolyl, isoxazolyl, symmetrical and unsymmetrical triazolyl, pyrrolyl, furanyl, diazenyl, triazenyl, 1,2,4-triazolone, 4,5-dihydroimidazolyl, and 1,4,5,6-tetrahydropyrimidinyl, wherein each is optionally substituted at any available nitrogen, that is capable of forming a bond, by $R^A$ and optionally substituted at any available carbon by $R^3$, $R^{3'}$, and $R^4$; wherein the U≡Y and V≡Y bonds may be single, double, or aromatic. U is nitrogen, $NR^A$, S, or O. V is nitrogen, carbon or CH. Y is carbon or CH.

$R^A$ is chosen from hydrogen, $(C_1-C_6)$alkyl, optionally substituted aryl, and optionally substituted heteroaryl groups, said heteroaryl groups having from 1 to 3 rings, 5 to 7 ring members in each ring and, in at least one of said rings, from 1 to about 3 heteroatoms selected from N, O, and S.

$R^5$ and $R^6$ may be taken together to form a carbonyl group; or $R^5$ and $R^6$ are independently chosen from hydrogen, halogen, hydroxy, haloalkyl, haloalkoxy, nitro, cyano, —COOH, amino, $R_{10}$, —NH($R_{10}$), —N($R_{10}$) ($R_{11}$), —O($R_{10}$), —SO$_2$NH$_2$, —SO$_2$NH($R_{10}$) —SO$_2$N($R_{10}$)($R_{11}$), —NHCO($R_{10}$), —N($R_{10}$)CO($R_{11}$), —NHCO$_2$($R_{10}$), —N($R_{10}$)CO$_2$($R_{11}$), —NHSO$_2$($R_{10}$), —N($R_{10}$) SO$_2$($R_{11}$), —SO$_2$NHCO($R_{10}$), —SO$_2$N($R_{10}$)CO($R_{11}$), —CONHSO$_2$ ($R_{10}$), —CON($R_{10}$)SO$_2$($R_{10}$), —CONH$_2$, CONH($R_{10}$), —CON($R_{10}$)($R_{11}$), —CO$_2$($R_{10}$), —CO($R_{10}$), —SO$_{0-2}$($R_{10}$) optionally substituted aryl groups, and optionally substituted heteroaryl groups. $R^3$, $R^{3'}$, and $R^4$ are independently chosen at each occurrence, and carry the same definitions as $R^5$ and $R^6$.

$R_{10}$ and $R_{11}$ are independently chosen from straight, branched, and cyclic alkyl groups and (cycloalkyl)alkyl groups, said straight, branched, and cyclic alkyl groups and (cycloalkyl)alkyl groups consisting of 1 to 8 carbon atoms, and containing zero or one or more double or triple bonds, each of which 1 to 8 carbon atoms may be further substituted with one or more substituent(s) independently chosen from hydroxy, oxo, halogen, amino, mono or dialkylamino, cyano, nitro, alkoxy, —COOH, —SO$_2$NH$_2$, —SO$_2$NH($C_1-C_4$alkyl), —SO$_2$N($C_1-C_4$alkyl)($C_1-C_4$alkyl), —NHCO($C_1-C_4$alkyl), —N($C_1-C_4$alkyl)CO($C_1-C_4$alkyl), —NHCO$_2$($C_1-C_4$alkyl), —N($C_1-C_4$alkyl)CO$_2$($C_1-C_4$alkyl), —NHSO$_2$($C_1-C_4$alkyl), —N($C_1-C_4$alkyl)SO$_2$($C_1-C_4$alkyl), —SO$_2$N($C_1-C_4$alkyl)CO($C_1-C_4$alkyl), —SO$_2$NHCO($C_1-C_4$alkyl), —CON($C_1-C_4$alkyl) SO$_2$($C_1-C_4$alkyl), —CONHSO$_2$($C_1-C_4$alkyl), —CONH$_2$, —CONH($C_1-C_4$alkyl), —CON($C_1-C_4$alkyl)($C_1-C_4$alkyl), —CO$_2$($C_1-C_4$alkyl), —CO($C_1-C_4$alkyl), —SO$_{0-2}$($C_1-C_4$alkyl), $C_3-C_7$cycloalkyl, phenyl, pyridyl, pyrimidinyl, pyrazolyl, pyrrolyl, imidazolyl, thienyl, azetidinyl, pyrrolidinyl piperidinyl, piperazinyl, and morpholinyl groups.

Q represents a phenyl, naphthyl, quinolinyl, thienyl, pyridyl, pyrimidinyl, pyrazinyl, oxazolyl, isoxazolyl, symmetrical or unsymmetrical oxadiazolyl, symmetrical or unsymmetrical thiadiazolyl, symmetrical or unsymmetrical triazolyl, pyrrolyl, imidazolyl, pyrazolyl, furanyl, diazenyl, triazenyl, or triazolopyrazinyl group, each of which may be unsubstituted or substituted with up to three substituents independently selected from i) and ii) wherein i) represents hydroxy, cyano, halogen, nitro, amino, mono- or di-($C_1-C_6$) alkylamino, ($C_2-C_6$)alkenyl, ($C_2-C_6$)alkynyl, ($C_1-C_6$) alkoxy, trifluoromethyl, or trifluoromethoxy; ii) represents straight or branched chain ($C_1-C_6$)alkyl optionally containing heteroatoms and optionally substituted with one or more carbocyclic or heterocyclic group.

W is hydrogen, oxygen, $NR^7$, sulfur, or $CR^7R^8$ where $R^7$ and $R^8$ are the same or different and represent hydrogen, straight or branched chain ($C_1-C_6$)alkyl, or $CR^7R^8$ represent a $C_3-C_7$cycloalkyl group. When W is hydrogen, m is 0 and Z is absent.

Z is absent, hydrogen, hydroxy, straight or branched chain ($C_1-C_6$)alkoxy, ($C_3-C_7$)cycloalkyl, ($C_3-C_7$)cycloalkyl ($C_1-C_3$)alkoxy, amino, mono or di($C_1-C_6$)alkylamino, a non-aromatic carbocyclic, a non-aromatic heterocyclic group, or $NR_{12}COR_{13}$, where $R_{12}$ and $R_{13}$ are the same or different and represent hydrogen or straight or branched chain ($C_1-C_6$)alkyl, or $R_{12}$ and $R_{13}$ may be joined to form a 3 to 8 membered heterocycloalkyl ring, or Z is a phenyl, napthyl, quinolinyl, thienyl, thiazolyl, pyridyl, pyrimidinyl, imidazolyl, pyrazolyl, pyrazinyl, pyridizinyl, piperidinyl, oxazolyl, isoxazolyl, symmetrical or unsymmetrical thiadiazolyl, symmetrical or unsymmetrical triazolyl, symmetrical or unsymmetrical oxadiazolyl, pyrrolyl, furanyl, pyrimidinyl, diazenyl, triazenyl, 1,2,4-triazolone, 4,5-dihydroimidazolyl, or 1,4,5,6-tetrahydropyrimidinyl group.

The groups

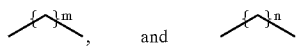

represent methylene groups which may be unsubstituted or substituted with halogen, cyano, nitro, amino, mono or di ($C_1$–$C_6$)alkylamino, ($C_2$–$C_6$)alkenyl, ($C_2$–$C_6$)alkynyl, ($C_1$–$C_6$)alkoxy, trifluoromethyl, trifluoromethoxy, straight or branched chain ($C_1$–$C_6$)alkyl, or ($C_3$–$C_7$)cycloalkyl, where m is 0, 1, 2, or 3; and n is 0, 1, 2, or 3.

Such compounds and pharmaceutically acceptable salts will be referred to as compounds and salts of Formula IA.

The invention includes, as another embodiment, compounds and salts of Formula IA in which $R^3$, $R^{3'}$, $R^4$, $R^5$, and $R^6$ are independently chosen from hydrogen, halogen, hydroxy, nitro, cyano, amino, —COOH, ($C_1$–$C_4$)alkyl, halo ($C_1$–$C_2$)alkyl, halo($C_1$–$C_2$)alkoxy, mono- and di-($C_1$–$C_4$) alkylamino, and $C_1$–$C_4$alkoxy.

The invention also relates to compounds of Formula I and the pharmaceutically acceptable salts thereof, where E is one or two saturated carbon atoms, $R^5$ and $R^6$ are hydrogen or alkyl, Y an V are carbon, and Q, W, Z, m and n are defined for Formula I.

The invention specifically embraces compounds of Formulae II–VII.

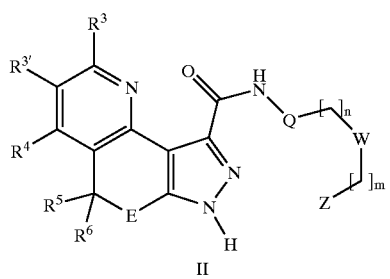

II

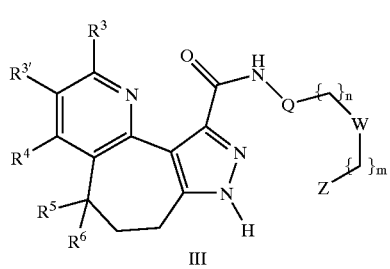

III

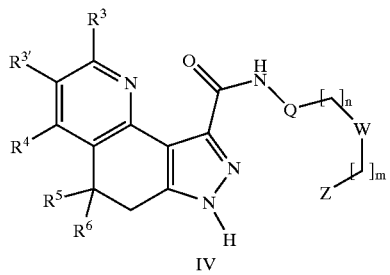

IV

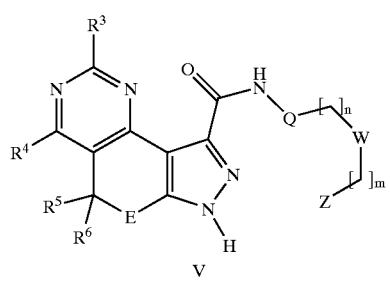

V

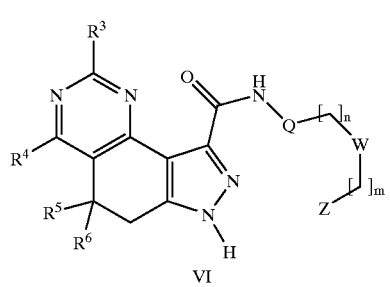

VI

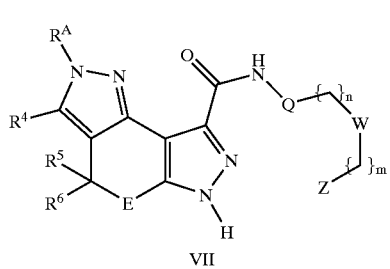

VII

Certain embodiments of the invention include compounds and salts of Formula II, V, and VII in which E is $(R^1R^2)_k$, k is 1 or 2, and $R^1$ and $R^2$ are independently hydrogen or methyl. In other embodiments the invention $R^1$ and $R^2$ are hydrogen.

The invention includes compounds and salts of Formula II–VII in which $R^3$, $R^{3'}$, $R^4$, $R^5$, and $R^6$, are independently chosen from hydrogen, halogen, amino, hydroxy, methyl, ethyl, methoxy, and ethoxy. In other embodiments $R^3$, $R^{3'}$, $R^4$, $R^5$, and $R^6$ in Formulae II–VII are independently hydrogen or methyl. In certain other embodiments $R^3$, $R^{3'}$, $R^4$, $R^5$, and $R^6$ are all hydrogen.

The invention pertains to compounds and salts of Formulae II–VII in which the group Q is phenyl, pyridyl, pyrimidinyl, thienyl, pyrrolyl, pyrazolyl, or imidazolyl, each of which may be substituted or unsubstituted. Q is preferably substituted by the group:

and may be further substituted by substituents that are preferably chosen from halogen, hydroxy, haloalkyl, haloalkoxy, alkoxy, alkyl, and cyano.

The invention also includes compounds and salts of Formula II–VII in which the group Q is phenyl, pyridyl, pyrimidinyl, thienyl, pyrrolyl, pyrazolyl, or imidazolyl, each of which may be substituted or unsubstituted and W is oxygen, NH, or $CH_2$.

The invention further includes compounds and salts of Formulae II–VII in which Z is hydrogen, hydroxy, straight or branched chain $(C_1-C_6)$alkoxy, $(C_3-C_7)$cycloalkyl, $(C_3-C_7)$cycloalkyl$(C_1C_3)$alkoxy, amino, mono or di-$(C_1-C_6)$alkylamino, $C_3-C_7$cycloalkyl, azetidinyl, pyrrolidinyl, morpholinyl, piperazinyl, or piperidinyl, or $NR_{12}COR_{13}$, where $R_{12}$ and $R_{13}$ are the same or different and represent hydrogen or straight or branched chain $(C_1-C_6)$alkyl, or $R_{12}$ and $R_{13}$ may be joined to form a 3 to 8 membered heterocycloalkyl ring, or Z is a phenyl, thienyl, thiazolyl, pyridyl, pyrimidinyl, imidazolyl, pyrazolyl, pyridizinyl, oxazolyl, isoxazolyl, symmetrical or unsymmetrical thiadiazolyl, symmetrical or unsymmetrical triazolyl, symmetrical or unsymmetrical oxadiazolyl, pyrrolyl, furanyl, pyrimidinyl, diazenyl, or triazinyl group.

The invention also includes compounds and salts of Formulae II–VII in which Z is hydrogen, hydroxy, straight or branched chain $(C_1-C_6)$alkoxy, $(C_3-C_7)$ cycloalkyl, $(C_3-C_7)$cycloalkyl$(C_1-C_3)$alkoxy, amino, mono or di-$(C_1-C_6)$alkylamino, $C_3-C_7$cycloalkyl, azetidinyl, pyrrolidinyl, morpholinyl, piperazinyl, or piperidinyl.

The invention pertains to compounds and salts of Formula VII in which E is $CR^1R^2$ and $R^1$ and $R^2$ are independently hydrogen or methyl.

In a yet another embodiment the invention pertains to compounds and salts of Formula VII in which: E is $CH_2$; $R^A$ is $(C_1-C_6)$alkyl, phenyl, thienyl, pyridyl, pyrimidinyl, pyrrolyl, or imidazolyl; and $R^4$, $R^5$, and $R^6$ are independently hydrogen, halogen, amino, hydroxy, methyl, ethyl, methoxy, or ethoxy.

The invention also includes compounds and salts of Formula VII in which E is $CH_2$; $R^4$, $R^5$, and $R^6$ are independently hydrogen; and $R^A$ is methyl, ethyl, or pyridyl.

The invention further includes compounds of the formula I-1:

I-1 and pharmaceutically acceptable salts thereof, wherein

X is hydrogen, $C_1-C_6$ alkyl, $C_1-C_6$ alkoxy, halogen, hydroxy, cyano, nitro, amino, mono- or di-$(C_1-C_6)$alkylamino, $C_2-C_6$alkenyl, $C_2-C_6$alkynyl, $C_1-C_6$ haloalkyl, $C_1-C_6$ haloalkoxy, amino$(C_1-C_6)$alkyl, mono- or di$(C_1-C_6)$ alkylamino$(C_1-C_6)$alkyl;

W is hydrogen, oxygen, $NR^7$, sulfur, or $CR^7R^8$ where $R^7$ and $R^8$ are the same or different and represent hydrogen, straight or branched chain alkyl, or $CR^7R^8$ represents a cycloalkyl group having from 3 to 7 carbon atoms, provided that when W is hydrogen, m is 0 and Z is absent;

Z is absent, hydrogen, hydroxy, straight or branched chain alkoxy, cycloalkyl, cycloalkyl(alkoxy), —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

and represent methylene groups which may be substituted with halogen, cyano, nitro, amino, mono or dialkylamino, alkenyl, alkynyl, alkoxy, trifluoromethyl, trifluoromethoxy, straight or branched chain alkyl, or cycloalkyl; and m and n are independently 0, 1, 2, or 3.

Preferred compounds of the formula I-1 include compounds of the formula I-1-a:

I-1-a wherein X, W, Z, m and n are as defined above for formula I-1.

Preferred compounds of the formula I-1-a include compounds wherein:

X is hydrogen, $C_1-C_6$ alkyl, $C_1-C_6$ alkoxy, halogen, hydroxy, cyano, nitro, amino;

W is hydrogen, oxygen or $NR^7$, where $R^7$ represents hydrogen, or straight or branched chain alkyl, provided that when W is hydrogen, m is 0 and Z is absent;

Z is absent, hydrogen, —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-1-a also include compounds wherein:

X is halogen;

W is oxygen or $NR^7$, where $R^7$ represents hydrogen, or straight or branched chain alkyl;

Z is —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-1-a also include compounds of the formulae:

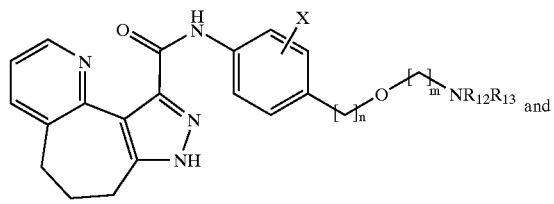

I-1-a-1

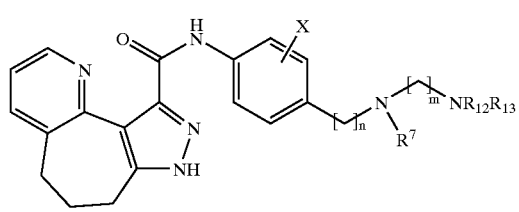

I-1-a-2 where X at each occurrence is independently hydrogen or halogen, and $R_{12}$ and $R_{13}$ at each occurrence are independently hydrogen or straight or branched chain alkyl, or $R_{12}$ and $R_{13}$ may be joined to form a heterocycloalkyl ring; m at each occurrence is independently 1, 2, or 3; and n at each occurrence is independently 0 or 1.

The invention further includes compounds of the formula I-2:

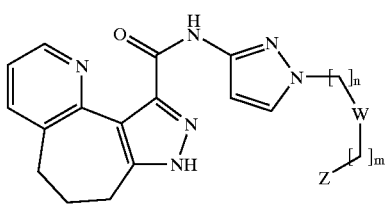

I-2 and pharmaceutically acceptable salts thereof, wherein

W is hydrogen, oxygen, $NR^7$, sulfur, or $CR^7R^8$ where $R^7$ and $R^8$ are the same or different and represent hydrogen, straight or branched chain alkyl, or $CR^7R^8$ represents a cycloalkyl group having from 3 to 7 carbon atoms, provided that when W is hydrogen, m is 0 and Z is absent;

Z is absent, hydrogen, hydroxy, straight or branched chain alkoxy, cycloalkyl, cycloalkyl(alkoxy), —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

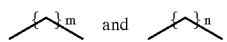

represent methylene groups which may be substituted with halogen, cyano, nitro, amino, mono or dialkylamino, alkenyl, alkynyl, alkoxy, trifluoromethyl, trifluoromethoxy, straight or branched chain alkyl, or cycloalkyl; and m and n are independently 0, 1, 2, or 3.

Preferred compounds of the formula I-2 include compounds wherein:

W is $CR^7R^8$ where $R^7$ and $R^8$ are the same or different and represent hydrogen, or straight or branched chain alkyl;

Z is —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 2 or 3; and n is 0 or 1.

Preferred compounds of the formula I-2 also include compounds wherein:

W is $CR^7R^8$ where $R^7$ and $R_8$ represent hydrogen;

Z is —$NR_{12}R_{13}$, where $R_{12}$ and $R_{13}$ are the same or different and represent hydrogen or straight or branched chain alkyl, or $R_{12}$ and $R_{13}$ may be joined to form a heterocycloalkyl ring;

m is 1, 2 or 3; and n is 0 or 1.

Preferred compounds of the formula I-2 also include compounds of the formula I-2-a:

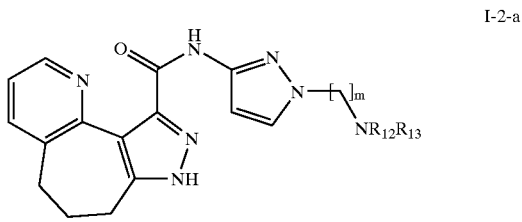

I-2-a wherein $R_{12}$ and $R_{13}$ are the same or different and represent hydrogen or straight or branched chain alkyl, or $R_{12}$ and $R_{13}$ may be joined to form a heterocycloalkyl ring; and m is 1, 2, or 3.

The invention further includes compounds of the formula I-3:

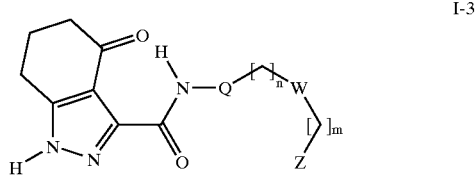

I-3 and pharmaceutically acceptable salts thereof, wherein

Q is phenyl, pyridinyl, or pyrimadinyl, each of which is optionally substituted with $C_1$–$C_6$ alkyl, $C_1$–$C_6$ alkoxy, halogen, hydroxy, cyano, nitro, amino, mono- or di-($C_1$–$C_6$) alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono- or di($C_1$–$C_6$) alkylamino($C_1$–$C_6$)alkyl;

W is hydrogen, oxygen, $NR^7$, sulfur, or $CR^7R^8$ where $R^7$ and $R^8$ are the same or different and represent hydrogen, straight or branched chain alkyl, or $CR^7R^8$ represents a cycloalkyl group having from 3 to 7 carbon atoms, provided that when W is hydrogen, m is 0 and Z is absent;

Z is absent, hydrogen, hydroxy, straight or branched chain alkoxy, cycloalkyl, cycloalkyl(alkoxy), —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

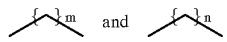

represent methylene groups which may be substituted with halogen, cyano, nitro, amino, mono or dialkylamino, alkenyl, alkynyl, alkoxy, trifluoromethyl, trifluoromethoxy, straight or branched chain alkyl, or cycloalkyl; and m and n are independently 0, 1, 2, or 3.

Preferred compounds of the formula I-3 include compounds of the formula I-3-a:

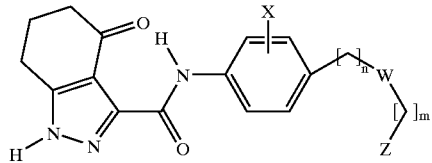

I-3-a wherein X is hydrogen, $C_1$–$C_6$ alkyl, $C_1$–$C_6$ alkoxy, halogen, hydroxy, cyano, nitro, amino, mono- or di-($C_1$–$C_6$) alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono- or di($C_1$–$C_6$) alkylamino($C_1$–$C_6$)alkyl; and W, Z, m and n are as defined above for formula I-3.

Preferred compounds of the formula I-3-a include compounds wherein:

X is hydrogen, $C_1$–$C_6$ alkyl, $C_1$–$C_6$ alkoxy, halogen, hydroxy, cyano, nitro, amino;

W is hydrogen, oxygen or $NR^7$, where $R^7$ represents hydrogen, or straight or branched chain alkyl, provided that when W is hydrogen, m is 0 and Z is absent;

Z is absent, hydrogen, —$NR_{12}R_{13}$ or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-3-a also include compounds wherein:

X is halogen;

W is oxygen or $NR^7$, where $R^7$ represents hydrogen, or straight or branched chain alkyl;

Z is —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-3-a also include compounds of the formula:

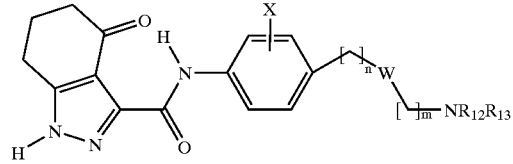

I-3-a-1 wherein W is O or —$NR^7$ where $R^7$ represents hydrogen, or straight or branched chain alkyl;

X is hydrogen or halogen; and $R_{12}$ and $R_{13}$ are independently hydrogen or straight or branched chain alkyl, or $R_{12}$ and $R_{13}$ may be joined to form a heterocycloalkyl ring;

m is 1, 2 or 3; and n is 0 or 1.

Preferred compounds of the formula I-3 also include compounds of the formula I-3-b:

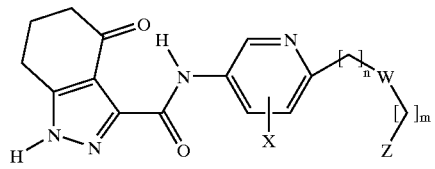

I-3-b wherein X is hydrogen, $C_1$–$C_6$ alkyl, $C_1$–$C_6$ alkoxy, halogen, hydroxy, cyano, nitro, amino, mono- or di-($C_1$–$C_6$) alkylamino, $C_2$–$C_6$alkenyl, $C_2$–$C_6$alkynyl, $C_1$–$C_6$ haloalkyl, $C_1$–$C_6$ haloalkoxy, amino ($C_1$–$C_6$) alkyl, mono- or di ($C_1$–$C_6$)alkylamino($C_1$–$C_6$)alkyl; and W, Z, m and n are as defined above for formula I-3.

Preferred compounds of the formula I-3-b include compounds wherein:

X is hydrogen, $C_1$–$C_6$ alkyl, $C_1$–$C_6$ alkoxy, halogen, hydroxy, cyano, nitro, amino;

W is hydrogen, oxygen or $NR^7$, where $R^7$ represents hydrogen, or straight or branched chain alkyl, provided that when W is hydrogen, m is 0 and Z is absent;

Z is absent, hydrogen, —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-3-b also include compounds wherein:

X is halogen;

W is oxygen or $NR^7$, where $R^7$ represents hydrogen, or straight or branched chain alkyl;

Z is —$NR_{12}R_{13}$, or $NR_{12}COR_{13}$ where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-3-b also include compounds of the formula:

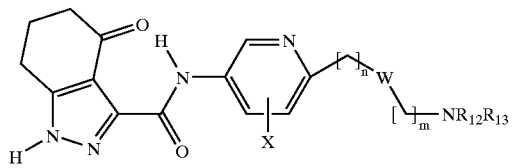

I-3-b-1 wherein W is O or —NR$^7$ where R$^7$ represents hydrogen, or straight or branched chain alkyl;

X is hydrogen or halogen; and

R$_{12}$ and R$_{13}$ are independently hydrogen or straight or branched chain alkyl, or R$_{12}$ and R$_{13}$ may be joined to form a heterocycloalkyl ring;

m is 1, 2 or 3; and n is 0 or 1.

The invention further includes compounds of the formula I-4:

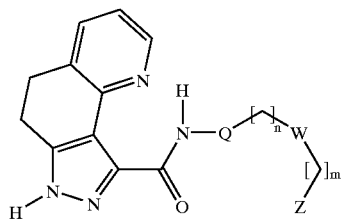

I-4 and pharmaceutically acceptable salts thereof, wherein

Q is phenyl, pyridinyl, or pyrimadinyl, each of which is optionally substituted with C$_1$–C$_6$ alkyl, C$_1$–C$_6$ alkoxy, halogen, hydroxy, cyano, nitro, amino, mono- or di-(C$_1$–C$_6$) alkylamino, C$_2$–C$_6$alkenyl, C$_2$–C$_6$alkynyl, C$_1$–C$_6$ haloalkyl, C$_1$–C$_6$ haloalkoxy, amino(C$_1$–C$_6$)alkyl, mono- or di(C$_1$–C$_6$) alkylamino(C$_1$–C$_6$)alkyl;

W is hydrogen, oxygen, NR$^7$, sulfur, or CR$^7$R$^8$ where R$^7$ and R$^8$ are the same or different and represent hydrogen, straight or branched chain alkyl, or CR$^7$R$^8$ represents a cycloalkyl group having from 3 to 7 carbon atoms, provided that when W is hydrogen, m is 0 and Z is absent;

Z is absent, hydrogen, hydroxy, straight or branched chain alkoxy, cycloalkyl, cycloalkyl(alkoxy), —NR$_{12}$R$_{13}$, or NR$_{12}$COR$_{13}$, where R$_{12}$ and R$_{13}$ are the same or different and represent hydrogen or straight or branched chain alkyl, or R$_{12}$ and R$_{13}$ may be joined to form a heterocycloalkyl ring, or Z is an optionally substituted carbocyclic or optionally substituted heterocyclic group;

 and 

represent methylene groups which may be substituted with halogen, cyano, nitro, amino, mono or dialkylamino, alkenyl, alkynyl, alkoxy, trifluoromethyl, trifluoromethoxy, straight or branched chain alkyl, or cycloalkyl; and m and n are independently 0, 1, 2, or 3.

Preferred compounds of the formula I-4 include compounds of the formula I-4-a:

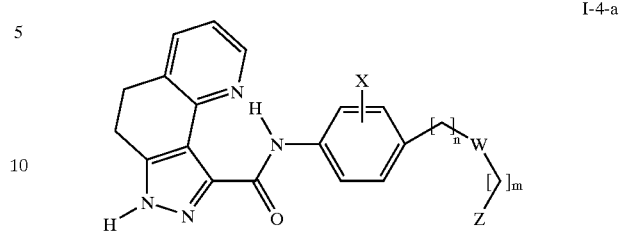

I-4-a wherein X is hydrogen, C$_1$–C$_6$ alkyl, C$_1$–C$_6$ alkoxy, halogen, hydroxy, cyano, nitro, amino, mono- or di-(C$_1$–C$_6$) alkylamino, C$_2$–C$_6$alkenyl, C$_2$–C$_6$alkynyl, C$_1$–C$_6$ haloalkyl, C$_1$–C$_6$ haloalkoxy, amino(C$_1$–C$_6$)alkyl, mono- or di(C$_1$–C$_6$) alkylamino(C$_1$–C$_6$)alkyl; and W, Z, m and n are as defined above for formula I-4.

Preferred compounds of the formula I-4-a include compounds wherein:

X is hydrogen, C$_1$–C$_6$ alkyl, C$_1$–C$_6$ alkoxy, halogen, hydroxy, cyano, nitro, amino;

W is hydrogen, oxygen or NR$^7$, where R$^7$ represents hydrogen, or straight or branched chain alkyl, provided that when W is hydrogen, m is 0 and Z is absent;

Z is absent, hydrogen, —NR$_{12}$R$_{13}$, or NR$_{12}$COR$_{13}$, where R$_{12}$ and R$_{13}$ are the same or different and represent hydrogen or straight or branched chain alkyl, or R$_{12}$ and R$_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-4-a also include compounds wherein:

X is halogen;

W is oxygen or NR$^7$, where R$^7$ represents hydrogen, or straight or branched chain alkyl;

Z is —NR$_{12}$R$_{13}$, or NR$_{12}$COR$_{13}$, where R$_{12}$ and R$_{13}$ are the same or different and represent hydrogen or straight or branched chain alkyl, or R$_{12}$ and R$_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-4-a also include compounds of the formula:

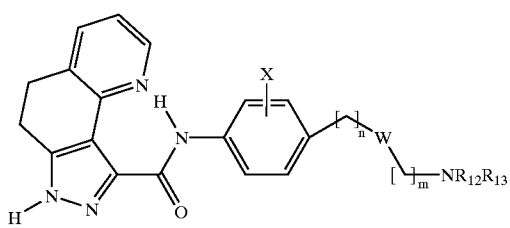

I-4-a-1 wherein W is O or —NR$^7$ where R$^7$ represents hydrogen, or straight or branched chain alkyl;

X is hydrogen or halogen;

R$_{12}$ and R$_{13}$ are independently hydrogen or straight or branched chain alkyl, or R$_{12}$ and R$_{13}$ may be joined to form a heterocycloalkyl ring;

m is 1, 2 or 3; and n is 0 or 1.

Preferred compounds of the formula I-4 also include compounds of the formula I-4-b:

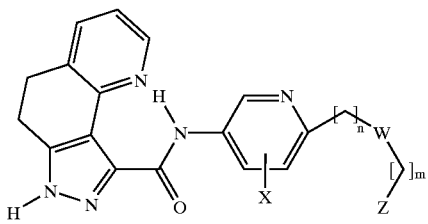

I-4-b wherein X is hydrogen, $C_1$–$C_6$ alkyl, $C_1$–$C_6$ alkoxy, halogen, hydroxy, cyano, nitro, amino, mono- or di-($C_1$–$C_6$) alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono- or di($C_1$–$C_6$) alkylamino($C_1$–$C_6$)alkyl; and W, Z, m and n are as defined above for formula I-4.

Preferred compounds of the formula I-4-b include compounds wherein:

X is hydrogen, $C_1$–$C_6$ alkyl, $C_1$–$C_6$ alkoxy, halogen, hydroxy, cyano, nitro, amino;

W is hydrogen, oxygen or $NR^7$, where $R^7$ represents hydrogen, or straight or branched chain alkyl, provided that when W is hydrogen, m is 0 and Z is absent;

Z is absent, hydrogen, —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-4-b also include compounds wherein:

X is halogen;

W is oxygen or $NR^7$, where $R^7$ represents hydrogen, or straight or branched chain alkyl;

Z is —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-4-b also include compounds of the formula:

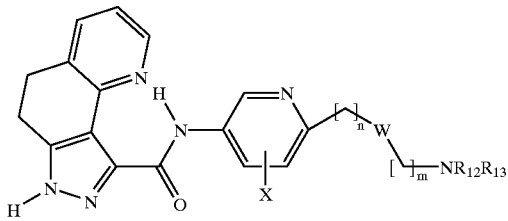

I-4-b-1 wherein W is O or —$NR^7$ where $R^7$ represents hydrogen, or straight or branched chain alkyl;

X is hydrogen or halogen;

$R_{12}$ and $R_{13}$ are independently hydrogen or straight or branched chain alkyl, or $R_{12}$ and $R_{13}$ may be joined to form a heterocycloalkyl ring;

m is 1, 2 or 3; and n is 0 or 1.

The invention further includes compounds of the formula I-5:

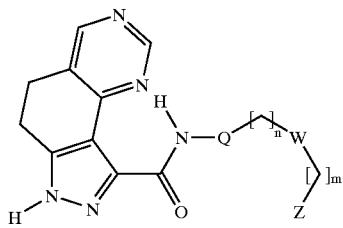

I-5 and pharmaceutically acceptable salts thereof, wherein

Q is phenyl, pyridinyl, or pyrimadinyl, each of which is optionally substituted with $C_1$–$C_6$ alkyl, $C_1$–$C_6$ alkoxy, halogen, hydroxy, cyano, nitro, amino, mono- or di-($C_1$–$C_6$) alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono- or di($C_1$–$C_6$) alkylamino($C_1$–$C_6$)alkyl;

W is hydrogen, oxygen, $NR^7$, sulfur, or $CR^7R^8$ where $R^7$ and $R^8$ are the same or different and represent hydrogen, straight or branched chain alkyl, or $CR^7R^8$ represents a cycloalkyl group having from 3 to 7 carbon atoms, provided that when W is hydrogen, m is 0 and Z is absent;

Z is absent, hydrogen, hydroxy, straight or branched chain alkoxy, cycloalkyl, cycloalkyl(alkoxy), —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

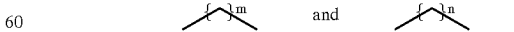

represent methylene groups which may be substituted with halogen, cyano, nitro, amino, mono or dialkylamino, alkenyl, alkynyl, alkoxy, trifluoromethyl, trifluoromethoxy, straight or branched chain alkyl, or cycloalkyl; and m and n are independently 0, 1, 2, or 3.

Preferred compounds of the formula I-5 include compounds of the formula I-5-a:

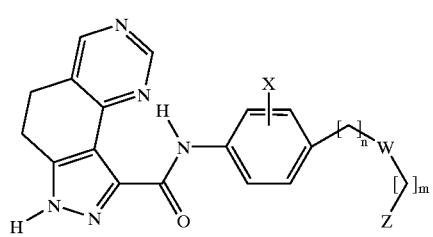

I-5-a wherein X is hydrogen, $C_1$–$C_6$ alkyl, $C_1$–$C_6$ alkoxy, halogen, hydroxy, cyano, nitro, amino, mono- or di-($C_1$–$C_6$) alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono- or di($C_1$–$C_6$) alkylamino($C_1$–$C_6$)alkyl; and W, Z, m and n are as defined above for formula I-5.

Preferred compounds of the formula I-5-a include compounds wherein:

X is hydrogen, $C_1$–$C_6$ alkyl, $C_1$–$C_6$ alkoxy, halogen, hydroxy, cyano, nitro, amino;

W is hydrogen, oxygen or $NR^7$, where $R^7$ represents hydrogen, or straight or branched chain alkyl, provided that when W is hydrogen, m is 0 and Z is absent;

Z is absent, hydrogen, —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-5-a also include compounds wherein:

X is halogen;

W is oxygen or $NR^7$, where $R^7$ represents hydrogen, or straight or branched chain alkyl;

Z is —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-5-a also include compounds of the formula:

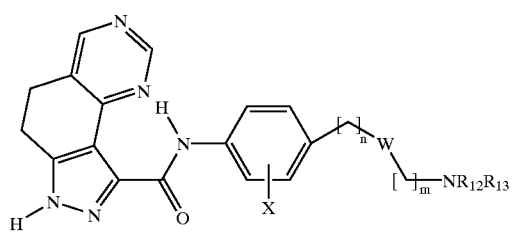

I-5-a-1 wherein W is O or —$NR^7$ where $R^7$ represents hydrogen, or straight or branched chain alkyl;

X is hydrogen or halogen;

$R_{12}$ and $R_{13}$ are independently hydrogen or straight or branched chain alkyl, or $R_{12}$ and $R_{13}$ may be joined to form a heterocycloalkyl ring;

m is 1, 2 or 3; and n is 0 or 1.

Preferred compounds of the formula I-5 also include compounds of the formula I-5-b:

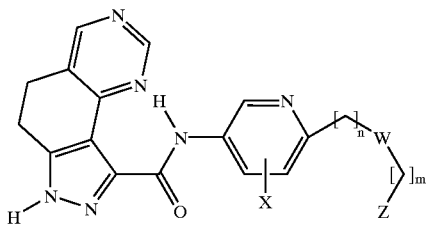

I-5-b wherein X is hydrogen, $C_1$–$C_6$ alkyl, $C_1$–$C_6$ alkoxy, halogen, hydroxy, cyano, nitro, amino, mono- or di-($C_1$–$C_6$) alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono- or di($C_1$–$C_6$) alkylamino($C_1$–$C_6$)alkyl; and W, Z, m and n are as defined above for formula I-5.

Preferred compounds of the formula I-5-b include compounds wherein:

X is hydrogen, $C_1$–$C_6$ alkyl, $C_1$–$C_6$ alkoxy, halogen, hydroxy, cyano, nitro, amino;

W is hydrogen, oxygen or $NR^7$, where $R^7$ represents hydrogen, or straight or branched chain alkyl, provided that when W is hydrogen, m is 0 and Z is absent;

Z is absent, hydrogen, —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-5-b also include compounds wherein:

X is halogen;

W is oxygen or $NR^7$, where $R^7$ represents hydrogen, or straight or branched chain alkyl;

Z is —$NR_{12}R_{13}$, or $NR_{12}COR_{13}$ where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-5-b also include compounds of the formula:

I-5-b-1

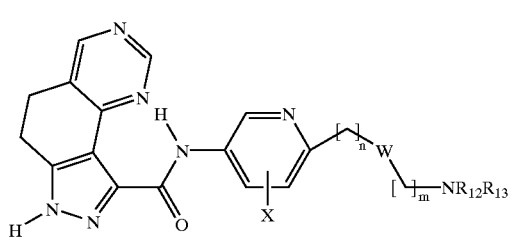

wherein W is O or —NR$^7$ where R$^7$ represents hydrogen, or straight or branched chain alkyl;

X is hydrogen or halogen;

R$_{12}$ and R$_{13}$ are independently hydrogen or straight or branched chain alkyl, or R$_{12}$ and R$_{13}$ may be joined to form a heterocycloalkyl ring;

m is 1, 2 or 3; and n is 0 or 1.

The invention further includes compounds of the formula I-6:

I-6

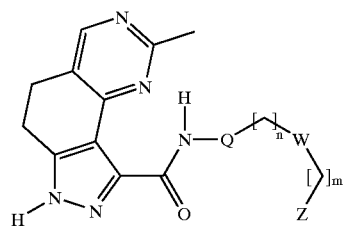

and pharmaceutically acceptable salts thereof, wherein

Q is phenyl, pyridinyl, or pyrimadinyl, each of which is optionally substituted with C$_1$–C$_6$ alkyl, C$_1$–C$_6$ alkoxy, halogen, hydroxy, cyano, nitro, amino, mono- or di-(C$_1$–C$_6$) alkylamino, C$_2$–C$_6$alkenyl, C$_2$–C$_6$alkynyl, C$_1$–C$_6$ haloalkyl, C$_1$–C$_6$ haloalkoxy, amino(C$_1$–C$_6$)alkyl, mono- or di(C$_1$–C$_6$) alkylamino(C$_1$–C$_6$)alkyl;

W is hydrogen, oxygen, NR$^7$, sulfur, or CR$^7$R$^8$ where R$^7$ and R$^8$ are the same or different and represent hydrogen, straight or branched chain alkyl, or CR$^7$R$^8$ represents a cycloalkyl group having from 3 to 7 carbon atoms, provided that when W is hydrogen, m is 0 and Z is absent;

Z is absent, hydrogen, hydroxy, straight or branched chain alkoxy, cycloalkyl, cycloalkyl(alkoxy), —NR$_{12}$R$_{13}$, or NR$_{12}$COR$_{13}$, where R$_{12}$ and R$_{13}$ are the same or different and represent hydrogen or straight or branched chain alkyl, or R$_{12}$ and R$_{13}$ may be joined to form a heterocycloalkyl ring, or Z is an optionally substituted carbocyclic or optionally substituted heterocyclic group;

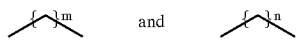

represent methylene groups which may be substituted with halogen, cyano, nitro, amino, mono or dialkylamino, alkenyl, alkynyl, alkoxy, trifluoromethyl, trifluoromethoxy, straight or branched chain alkyl, or cycloalkyl; and m and n are independently 0, 1, 2, or 3.

Preferred compounds of the formula I-6 include compounds of the formula I-6-a:

I-6-a

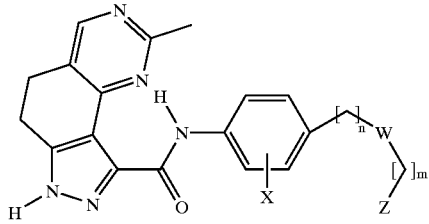

wherein X is hydrogen, C$_1$–C$_6$ alkyl, C$_1$–C$_6$ alkoxy, halogen, hydroxy, cyano, nitro, amino, mono- or di-(C$_1$–C$_6$) alkylamino, C$_2$–C$_6$alkenyl, C$_2$–C$_6$alkynyl, C$_1$–C$_6$ haloalkyl, C$_1$–C$_6$ haloalkoxy, amino (C$_1$–C$_6$) alkyl, mono- or di (C$_1$–C$_6$)alkylamino(C$_1$–C$_6$)alkyl; and W, Z, m and n are as defined above for formula I-6.

Preferred compounds of the formula I-6-a include compounds wherein:

X is hydrogen, C$_1$–C$_6$ alkyl, C$_1$–C$_6$ alkoxy, halogen, hydroxy, cyano, nitro, amino;

W is hydrogen, oxygen or NR$^7$, where R$^7$ represents hydrogen, or straight or branched chain alkyl, provided that when W is hydrogen, m is 0 and Z is absent;

Z is absent, hydrogen, —NR$_{12}$R$_{13}$, or NR$_{12}$COR$_{13}$, where R$_{12}$ and R$_{13}$ are the same or different and represent hydrogen or straight or branched chain alkyl, or R$_{12}$ and R$_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-6-a also include compounds wherein:

X is halogen;

W is oxygen or NR$^7$, where R$^7$ represents hydrogen, or straight or branched chain alkyl;

Z is —NR$_{12}$R$_{13}$, or NR$_{12}$COR$_{13}$ where R$_{12}$ and R$_{13}$ are the same or different and represent hydrogen or straight or branched chain alkyl, or R$_{12}$ and R$_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-6-a also include compounds of the formula:

I-6-a-1

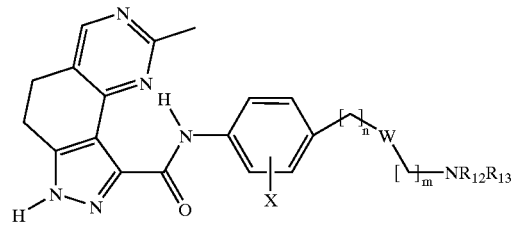

wherein W is O or —NR$^7$ where R$^7$ represents hydrogen, or straight or branched chain alkyl;

X is hydrogen or halogen;

R$_{12}$ and R$_{13}$ are independently hydrogen or straight or branched chain alkyl, or R$_{12}$ and R$_{13}$ may be joined to form a heterocycloalkyl ring;

m is 1, 2 or 3; and n is 0 or 1.

Preferred compounds of the formula I-6 also include compounds of the formula I-6-b:

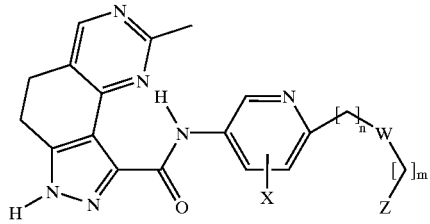

I-6-b wherein X is hydrogen, C$_1$–C$_6$ alkyl, C$_1$–C$_6$ alkoxy, halogen, hydroxy, cyano, nitro, amino, mono- or di-(C$_1$–C$_6$) alkylamino, C$_2$–C$_6$alkenyl, C$_2$–C$_6$alkynyl, C$_1$–C$_6$ haloalkyl, C$_1$–C$_6$ haloalkoxy, amino(C$_1$–C$_6$)alkyl, mono- or di(C$_1$–C$_6$) alkylamino(C$_1$–C$_6$)alkyl; and W, Z, m and n are as defined above for formula I-6.

Preferred compounds of the formula I-6-b include. compounds wherein:

X is hydrogen, C$_1$–C$_6$ alkyl, C$_1$–C$_6$ alkoxy, halogen, hydroxy, cyano, nitro, amino;

W is hydrogen, oxygen or NR$^7$, where R$^7$ represents hydrogen, or straight or branched chain alkyl, provided that when W is hydrogen, m is 0 and Z is absent;

Z is absent, hydrogen, —NR$_{12}$R$_{13}$, or NR$_{12}$COR$_{13}$, where R$_{12}$ and R$_{13}$ are the same or different and represent hydrogen or straight or branched chain alkyl, or R$_{12}$ and R$_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-6-b also include compounds wherein:

X is halogen;

W is oxygen or NR$^7$, where R$^7$ represents hydrogen, or straight or branched chain alkyl;

Z is —NR$_{12}$R$_{13}$, or NR$_{12}$COR$_{13}$, where R$_{12}$ and R$_{13}$ are the same or different and represent hydrogen or straight or branched chain alkyl, or R$_{12}$ and R$_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-6-b also include compounds of the formula:

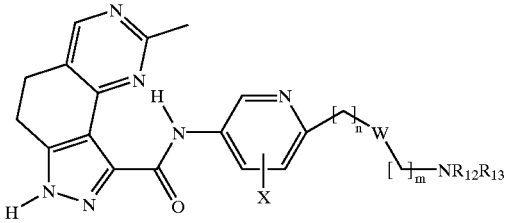

I-6-b-1 wherein W is O or —NR$^7$ where R$^7$ represents hydrogen, or straight or branched chain alkyl;

X is hydrogen or halogen;

R$_{12}$ and R$_{13}$ are independently hydrogen or straight or branched chain alkyl, or R$_{12}$ and R$_{13}$ may be joined to form a heterocycloalkyl ring;

m is 1, 2 or 3; and n is 0 or 1.

The invention further includes compounds of the formula I-7:

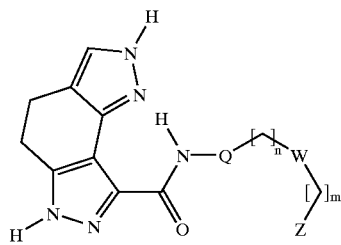

I-7 and pharmaceutically acceptable salts thereof, wherein

Q is phenyl, pyridinyl, or pyrimadinyl, each of which is optionally substituted with C$_1$–C$_6$ alkyl, C$_1$–C$_6$ alkoxy, halogen, hydroxy, cyano, nitro, amino, mono- or di-(C$_1$–C$_6$) alkylamino, C$_2$–C$_6$alkenyl, C$_2$–C$_6$alkynyl, C$_1$–C$_6$ haloalkyl, C$_1$–C$_6$ haloalkoxy, amino (C$_1$–C$_6$) alkyl, mono- or di (C$_1$–C$_6$)alkylamino(C$_1$–C$_6$)alkyl;

W is hydrogen, oxygen, NR$^7$, sulfur, or CR$^7$R$^8$ where R$^7$ and R$^8$ are the same or different and represent hydrogen, straight or branched chain alkyl, or CR$^7$R$^8$ represents a cycloalkyl group having from 3 to 7 carbon atoms, provided that when W is hydrogen, m is 0 and Z is absent;

Z is absent, hydrogen, hydroxy, straight or branched chain alkoxy, cycloalkyl, cycloalkyl(alkoxy), —NR$_{12}$R$_{13}$, or NR$_{12}$COR$_{13}$, where R$_{12}$ and R$_{13}$ are the same or different and represent hydrogen or straight or branched chain alkyl, or R$_{12}$ and R$_{13}$ may be joined to form a heterocycloalkyl ring, or Z is an optionally substituted carbocyclic or optionally substituted heterocyclic group;

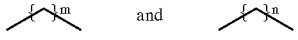

represent methylene groups which may be substituted with halogen, cyano, nitro, amino, mono or dialkylamino, alkenyl, alkynyl, alkoxy, trifluoromethyl, trifluoromethoxy, straight or branched chain alkyl, or cycloalkyl; and m and n are independently 0, 1, 2, or 3.

Preferred compounds of the formula I-7 include compounds of the formula I-7-a:

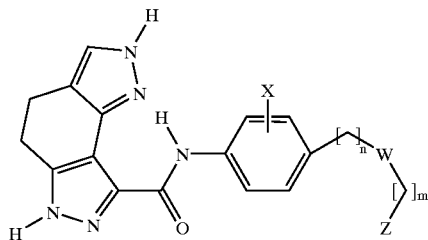

I-7-a wherein X is hydrogen, $C_1$–$C_6$ alkyl, $C_1$–$C_6$ alkoxy, halogen, hydroxy, cyano, nitro, amino, mono- or di-($C_1$–$C_6$) alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono- or di($C_1$–$C_6$) alkylamino($C_1$–$C_6$)alkyl; and W, Z, m and n are as defined above for formula I-7.

Preferred compounds of the formula I-7-a include compounds wherein:

X is hydrogen, $C_1$–$C_6$ alkyl, $C_1$–$C_6$ alkoxy, halogen, hydroxy, cyano, nitro, amino;

W is hydrogen, oxygen or $NR^7$, where $R^7$ represents hydrogen, or straight or branched chain alkyl, provided that when W is hydrogen, m is 0 and Z is absent;

Z is absent, hydrogen, —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-7-a also include compounds wherein:

X is halogen;

W is oxygen or $NR^7$, where $R^7$ represents hydrogen, or straight or branched chain alkyl;

Z is —$NR_{12}R_{13}$, or $NR_{12}COR_3$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-7-a also include compounds of the formula:

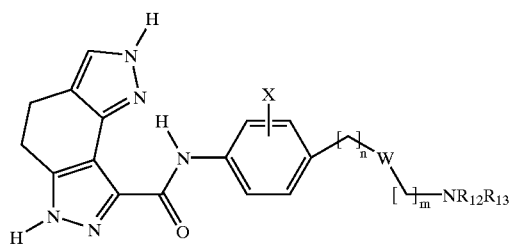

I-7-a-1 wherein W is O or —$NR^7$ where $R^7$ represents hydrogen, or straight or branched chain alkyl;

X is hydrogen or halogen;

$R_{12}$ and $R_{13}$ are independently hydrogen or straight or branched chain alkyl, or $R_{12}$ and $R_{13}$ may be joined to form a heterocycloalkyl ring;

m is 1, 2 or 3; and n is 0 or 1.

Preferred compounds of the formula I-7 also include compounds of the formula I-7-b:

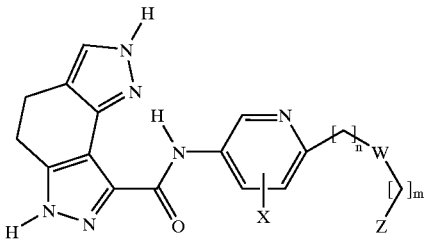

I-7-b wherein X is hydrogen, $C_1$–$C_6$ alkyl, $C_1$–$C_6$ alkoxy, halogen, hydroxy, cyano, nitro, amino, mono- or di-($C_1$–$C_6$) alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono- or di($C_1$–$C_6$) alkylamino($C_1$–$C_6$)alkyl; and W, Z, m and n are as defined above for formula I-7.

Preferred compounds of the formula I-7-b include compounds wherein:

X is hydrogen, $C_1$–$C_6$ alkyl, $C_1$–$C_6$ alkoxy, halogen, hydroxy, cyano, nitro, amino;

W is hydrogen, oxygen or $NR^7$, where $R^7$ represents hydrogen, or straight or branched chain alkyl, provided that when W is hydrogen, m is 0 and Z is absent;

Z is absent, hydrogen, —$NR_{12}R_{13}$, or $NR_{12}COR_{13}$ where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-7-b also include compounds wherein:

X is halogen;

W is oxygen or $NR^7$, where $R^7$ represents hydrogen, or straight or branched chain alkyl;

Z is —$NR_{12}R_{13}$, or $NR_{12}COR_{13}$, where $R_{12}$ and $R_{13}$ are the same or different and represent hydrogen or straight or branched chain alkyl, or $R_{12}$ and $R_{13}$ may be joined to form a heterocycloalkyl ring, or Z is an optionally substituted carbocyclic or optionally substituted heterocyclic group;

m is 1, 2 or 3; and n is 0 or 1.

Preferred compounds of the formula I-7-b also include compounds of the formula:

I-7-b-1

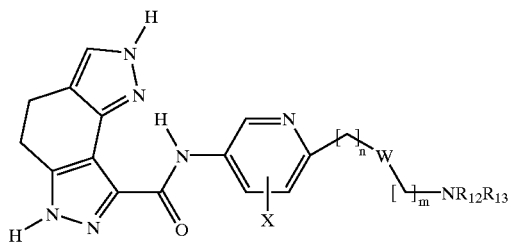

wherein W is O or —NR$^7$ where R$^7$ represents hydrogen, or straight or branched chain alkyl;

X is hydrogen or halogen;

R$_{12}$ and R$_{13}$ are independently hydrogen or straight or branched chain alkyl, or R$_{12}$ and R$_{13}$ may be joined to form a heterocycloalkyl ring;

m is 1, 2 or 3; and n is 0 or 1.

Also included in the invention are compounds of Formula VIII useful in synthesizing compounds of Formula I–VII.

Formula VIII

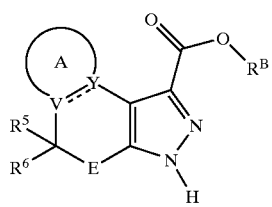

E in Formula VIII represents (CR$^1$R$^2$)$_k$, wherein R$^1$ and R$^2$ are independently chosen from hydrogen, halogen, hydroxy, cyano, nitro, amino, alkyl, alkenyl, alkynyl, haloalkyl, haloalkoxy, mono or dialkylamino, and alkoxy, where k is 0, 1, 2, or 3;

The group

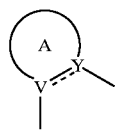

represents an optionally substituted saturated, partially unsaturated or aromatic heterocyclic ring having from 5 to 7 ring atoms, wherein from 1 to 4 ring atoms are selected from nitrogen, oxygen and sulfur and remaining ring atoms are carbon and the V═Y bond is a single, double, or aromatic bond. V is nitrogen, carbon, or CH. Y is carbon or CH.

R$^5$ and R$^6$ are taken together to form a carbonyl group; or R$^5$ and R$^6$ are independently chosen from hydrogen, halogen, hydroxy, haloalkyl, haloalkoxy, nitro, cyano, —COOH, amino, R$_{10}$, —NH(R$_{10}$), —N(R$_{10}$)(R$_{11}$), —O(R$_{10}$), —SO$_2$NH$_2$, —SO$_2$NH(R$_{10}$), —SO$_2$N(R$_{10}$)(R$_{11}$), —NHCO(R$_{10}$), —N(R$_{10}$)CO(R$_{11}$), —NHCO$_2$(R$_{10}$), —N(R$_{10}$)CO$_2$(R$_{11}$), —NHSO$_2$(R$_{10}$), —N(R$_{10}$)SO$_2$(R$_{11}$), —SO$_2$NHCO(R$_{10}$), —SO$_2$N(R$_{10}$)CO(R$_{11}$), —CONHSO$_2$(R$_{10}$), —CON(R$_{10}$)SO$_2$(R$_{11}$), —CONH$_2$, —CONH(R$_{10}$), —CON(R$_{10}$)(R$_{11}$), —CO$_2$(R$_{10}$), —CO(R$_{10}$), —SO$_{0-2}$(R$_{10}$), optionally substituted aryl, and optionally substituted heteroaryl.

R$_{10}$ and R$_{11}$ are independently chosen from straight, branched, and cyclic alkyl groups, and (cycloalkyl)alkyl groups, said straight, branched, and cyclic alkyl groups, and (cycloalkyl)alkyl groups consisting of 1 to 8 carbon atoms, and containing zero or one or more double or triple bonds, each of which 1 to 8 carbon atoms may be further substituted with one or more substituent(s) independently selected from hydroxy, oxo, halogen, amino, mono or dialkylamino, cyano, nitro, alkoxy, —COOH, —SO$_2$NH$_2$, —SO$_2$NH(alkyl), —SO$_2$N(alkyl) (alkyl), —NHCO(alkyl), —N(alkyl)CO(alkyl), —NHCO$_2$(alkyl), —N(alkyl)CO$_2$(alkyl), —NHSO$_2$(alkyl), —N(alkyl)SO$_2$(alkyl), —SO$_2$N(alkyl)CO (alkyl), —SO$_2$NHCO(alkyl), —CON(alkyl)SO$_2$(alkyl), —CONHSO$_2$(alkyl), —CONH$_2$, —CONH(alkyl), —CON (alkyl)(alkyl), —CO$_2$(alkyl), —CO(alkyl), —SO$_{0-2}$(alkyl), cycloalkyl, aryl, heteroaryl, and heterocycloalkyl.

R$^B$ is chosen from hydrogen, methyl, ethyl and benzyl.

Additionally the invention includes compounds of Formulae IX–XIV useful in the synthesis of compounds and salts of Formula I.

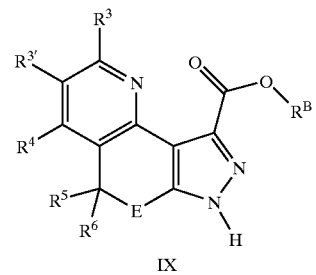

IX

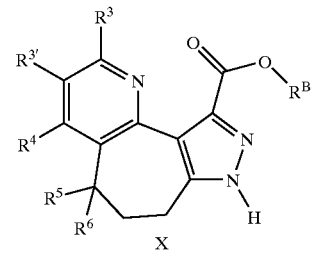

X

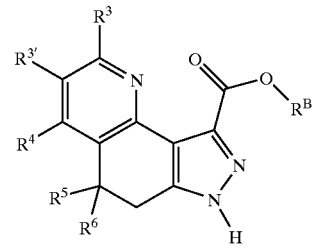

XI

-continued

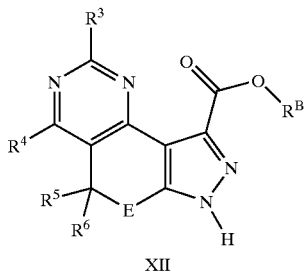

XII

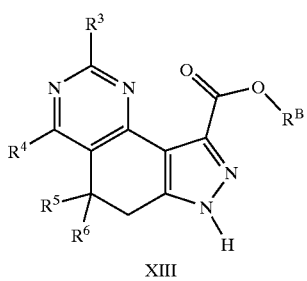

XIII

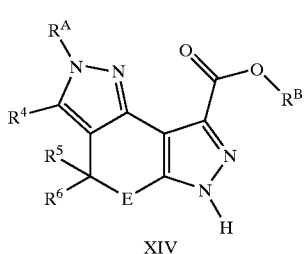

XIV

The invention provides compounds of Formulae IX–XIV in which $R^{3'}$, $R^4$, $R^5$, and $R^6$ are hydrogen and $R^3$ is chosen from $R^3$ is chosen from hydrogen, halogen, amino, hydroxy, methyl, ethyl, methoxy, and ethoxy.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The present invention also encompasses prodrugs of the compounds of Formula I.

The present invention also encompasses the acylated prodrugs of the compounds of Formula I. Those skilled in the art will recognize various synthetic methodologies, which may be employed to prepare non-toxic pharmaceutically acceptable addition salts and acylated prodrugs of the compounds encompassed by Formula I.

Additional Embodiments

This invention provides compounds, including provides substituted fused pyrazolecarboxylic acid arylamides, that bind with high selectivity to the benzodiazepine site of $GABA_A$ receptors, including human $GABA_A$ receptors. Preferred examples of the invention bind with high affinity to the benzodiazepine site of $GABA_A$ receptors, including human $GABA_A$ receptors. Without wishing to be bound to any particular theory, it is believed that the interaction of the compounds of Formula I with the benzodiazepine site results in the pharmaceutical utility of these compounds.

The invention provides methods for determining the presence or absence of $GABA_A$ receptors in a sample, comprising: a) contacting the sample with a compound or salt of Formula I, under conditions that permit binding of the compound to $GABA_A$ receptor; and b) detecting a level of compound bound to $GABA_A$ receptor, and therefrom determining the presence or absence of $GABA_A$ receptor in the sample. One example of such a method is provided in the binding assay given in Example 10.

In certain embodiments, such as the binding assay provided in Example 10, the compound is radiolabeled, and the step of detection comprises: (i) separating unbound compound from bound compound; and (ii) detecting the presence or absence of bound compound in the sample. The compound may also be fluorescently labeled or labeled with an indirect luminescent label.

The sample may be, for example, a tissue sample, tissue section, or preparation of cell membranes.

In certain embodiments the sample is a tissue section, and the labeled compound or salt is detected autoradiographically to generate an autoradiogram for each of the at least one samples. In these embodiments measurement of the amount of labeled compound or salt in the sample is carried out by viewing the autoradiograms and the comparison is a comparison of the exposure density of the autoradiograms.

The invention further comprises methods of treating patients in need of such treatment with an amount of a compound of the invention sufficient to alter the symptoms of a CNS disorder. Compounds of the inventions that act as agonists at $\alpha_2\beta_3\gamma_2$ and $\alpha_3\beta_3\gamma_2$ receptor subtypes are useful in treating anxiety disorders such as panic disorder, obsessive compulsive disorder and generalized anxiety disorder; stress disorders including post-traumatic stress, and acute stress disorders. Compounds of the inventions that act as agonists at $\alpha_2\beta_3\gamma_2$ and $\alpha_3\beta_3\gamma_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

The diseases and/or disorders that can also be treated using compounds and compositions according to the invention include:

Depression, e.g. depression, a typical depression, bipolar disorder, depressed phase of bipolar disorder.

Anxiety, e.g. general anxiety disorder (GAD), agoraphobia, panic disorder +/− agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g. sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g. cognition impairment, Alzheimer's disease, short-term memory deficits, especially short-term memory deficits associated with Alzheimer's disease, Parkinson's disease, mild cognitive impairment (MCI), age-related cognitive decline (ARCD), stroke, traumatic brain injury, AIDS associated dementia, and dementia associated with depression, anxiety or psychosis.

Attention Deficit Disorder, e.g. attention deficit disorder (ADD), and attention deficit and hyperactivity disorder (ADHD).

The invention also provides pharmaceutical compositions comprising compounds of the invention, including packaged pharmaceutical compositions for treating disorders responsive to $GABA_A$ receptor modulation, e.g., treatment of anxiety, depression, sleep disorders or cognitive impairment by $GABA_A$ receptor modulation. The packaged pharmaceutical compositions include a container holding a therapeutically effective amount of at least one $GABA_A$ receptor modulator as described supra and instructions (e.g., labeling) indicating the contained $GABA_A$ receptor ligand is to be used for treating a disorder responsive to $GABA_A$ receptor modulation in the patient.

In a separate aspect, the invention provides a method of potentiating the actions of other CNS active compounds, which comprises administering an effective amount of a compound of the invention in combination with another CNS active compound. Such CNS active compounds include, but are not limited to the following: for anxiety, serotonin receptor (e.g. $5-HT_{1A}$) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in a fashion analogous to that disclosed in Da-Rocha, et al., *J. Psychopharmacology* (1997) 11(3) 211–218; Smith, et al., *Am. J. Psychiatry* (1998) 155(10) 1339–45; or Le, et al., *Alcohol and Alcoholism* (1996) 31 Suppl. 127–132. Also see, the discussion of the use of the $GABA_A$ receptor ligand 3-(5-methylisoxazol-3-yl)-6-(1-methyl-1,2,3-triazol-4-yl)methyloxy-1,2,4-triazolo [3,4-a]phthalazine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of $GABA_A$ receptor ligands, 1,2,4-triazolo[4,3-b]pyridazines, in combination with SSRIs.

The present invention also pertains to methods of inhibiting the binding of benzodiazepine compounds, such as RO15-1788, to the $GABA_A$ receptors which methods involve contacting a compound of the invention with cells expressing $GABA_A$ receptors, wherein the compound is present at a concentration sufficient to inhibit benzodiazepine binding to $GABA_A$ receptors in vitro. This method includes inhibiting the binding of benzodiazepine compounds to $GABA_A$ receptors in vivo, e.g., in a patient given an amount of a compound of Formula I that would be sufficient to inhibit the binding of benzodiazepine compounds to $GABA_A$ receptors in vitro. In one embodiment, such methods are useful in treating benzodiazepine drug overdose. The amount of a compound that would be sufficient to inhibit the binding of a benzodiazepine compound to the $GABA_A$ receptor may be readily determined via an $GABA_A$ receptor binding assay, such as the assay described in Example 10. The $GABA_A$ receptors used to determine in vitro binding may be obtained from a variety of sources, for example from preparations of rat cortex or from cells expressing cloned human $GABA_A$ receptors.

The present invention also pertains to methods for altering the signal-transducing activity, particularly the chloride ion conductance of $GABA_A$ receptors, said method comprising exposing cells expressing such receptors to an effective amount of a compound of the invention. This method includes altering the signal-transducing activity of $GABA_A$ receptors in vivo, e.g., in a patient given an amount of a compound of Formula I that would be sufficient to alter the signal-transducing activity of $GABA_A$ receptors in vitro. The amount of a compound that would be sufficient to alter the signal-transducing activity of $GABA_A$ receptors may be determined via a $GABA_A$ receptor signal transduction assay, such as the assay described in Example 11.

The $GABA_A$ receptor ligands provided by this invention and labeled derivatives thereof are also useful as standards and reagents in determining the ability of a potential pharmaceutical to bind to the $GABA_A$ receptor.

Labeled derivatives of the $GABA_A$ receptor ligands provided by this invention are also useful as radiotracers for positron emission tomography (PET) imaging or for single photon emission computerized tomography (SPECT).

Pharmaceutical Preparations

The invention provides pharmaceutical compositions comprising a compound or pharmaceutically acceptable salt of Formula I, or any of the subformulae thereof, including Formulae II–VII in combination with at least one pharmaceutically acceptable carrier or excipient.

The pharmaceutical composition may be formulated as an injectable fluid, an aerosol, a cream, a gel, a pill, a capsule, a syrup, or a transdermal patch.

Those skilled in the art will recognize various synthetic methodologies that may be employed to prepare non-toxic pharmaceutically acceptable prodrugs of the compounds encompassed by Formula I. Those skilled in the art will also recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin-, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It may be convenient to formulate these animal feed and drinking water compositions so that the animal ingests an appropriate quantity of the composition during a meal or throughout the course of the day. It may also be convenient to present the composition as a premix for addition to the feed or drinking water.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have pharmacological properties that include, but are not limited to oral bioavailability, low toxicity, low serum protein binding, and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120–1127).

Preparation of Compounds

A general illustration of the preparation of compounds of Formula I in the present invention is given in Schemes I and II. The following abbreviations are used in the Schemes I and II and accompanying synthetic examples:

| ABBREVIATIONS USED | |
|---|---|
| DMFDMA | N,N-Dimethylformamide dimethyl acetal |
| MeOH | Methanol |
| NH₄OAc | Ammonium acetate |
| NaOAc | Sodium acetate |
| NBS | N-Bromosuccinimide |
| DCE | 1,2-Dichloroethane |
| DMF | N,N-Dimethylformamide |
| THF | Tetrahydrofuran |
| AcOH | Acetic acid |
| EtOAc | Ethyl acetate |
| EtOH | Ethanol |
| DMAP | 4-(Dimethylamino)pyridine |
| EDCI | 1-(3-Dimethylaminopropyl)-3-ethylcarbodiimide hydrochloride |

SCHEME I

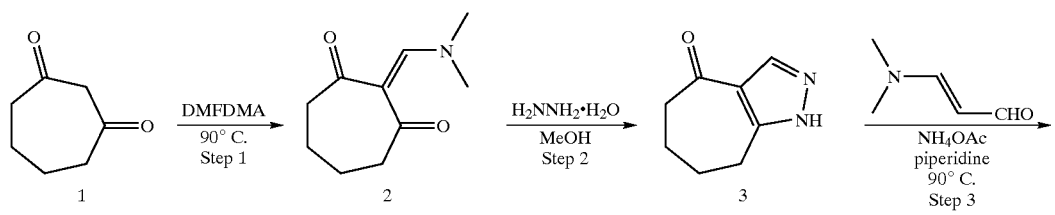

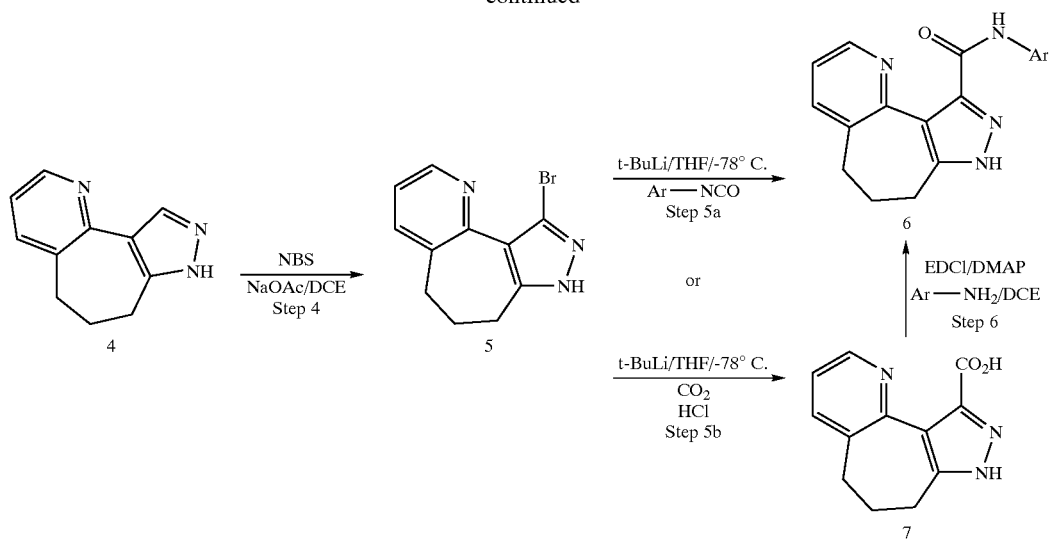

In Scheme I, Step 1, 1,3-cycloheptanedione is heated with excess N,N-Dimethylformamide dimethyl acetal to form enamine 2. In Step 2, treatment of 2 with hydrazine monohydrate in methanol provides fused pyrazole 3. Reaction of 3 with 3-(dimethylamino)-acrolein, piperidine and ammonium acetate in Step 3 provides tricyclic derivative 4. Bromination of 4 with N-bromosuccinimide in Step 4 provides the 3-bromopyrazole derivative 5. Bromopyrazole 5 is converted to the corresponding anilide derivative 6 in Step 5a by treatment at low temperature with excess t-butyllithium in tetrahydrofuran followed by treatment with an aryl isocyanate. Alternatively, the corresponding anilides are prepared from 5 by treatment with excess t-butyllithium in Step 5b followed by reaction with carbon dioxide to form carboxylic acid derivative 7. In Step 6, compound 7 is reacted with an aryl amine in the presence of an appropriate coupling agent (such as EDCI/DMAP) for form anilide 6. Those skilled in the art will recognize that this synthetic scheme can be easily adapted to produce a variety of compounds encompassed in the present invention. For example, a variety of different cyclic 1,3-diketones may be used to produce differently substituted derivatives of Formula I. As illustrated in Scheme II, intermediate 3 and related fused pyrazole ketones may be utilized to form a variety of fused tricylic systems via different heterocycle-forming sequences.

SCHEME II

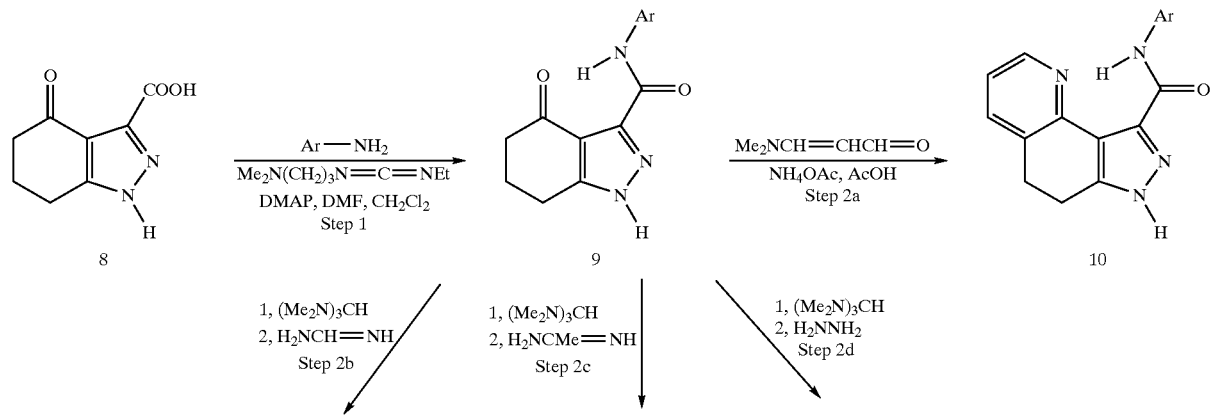

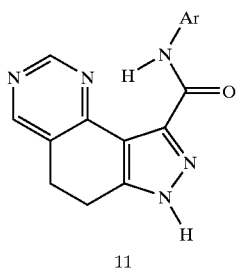
11

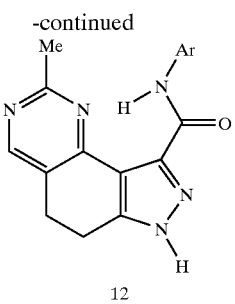
12

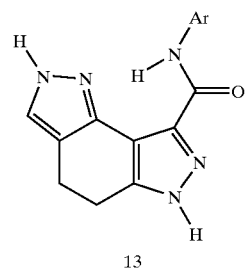
13

Ar = optionally substituted aryl or heteroaryl

The preparation of 4-oxo-4,5,6,7-tetrahydro-1H-indazole-3-carboxylic acid amides 9 used as intermediates in Scheme II, has been previously described (WO patent application no. 00/40565 which is hereby incorporated by reference at pages 16–25 for its teachings therein regarding the synthesis of 4-oxo-4,5,6,7-tetrahydro-1H-indazole-3-carboxylic acid amides). By analogy to Scheme I, amide 9 is converted to the corresponding fused pyridyl derivative 10 in Step 2a by reaction with 3-(dimethylamino)-acrolein and ammonium acetate in acetic acid. Generation of the corresponding enamine from 9 by heating with excess tris(dimethylamino)methane followed by reaction with formamidine (Step 2b), acetamidine (Step 2c) and hydrazine (Step 2c) provides the corresponding fused pyrimidine derivatives 11 and 12 and the corresponding pyrazole 13 respectively. Those skilled in the art will recognize that the reagents and starting materials employed in Scheme II can be readily modified to access a variety of additional compounds of Formula I.

Those skilled in the art will recognize that it may be necessary to utilize different solvents or reagents to achieve some of the above transformations. Unless otherwise specified all reagents and solvent are of standard commercial grade and are used without further purification. In some cases, depending on the particular compounds of Formula I that are desired, it may be necessary to modify Schemes I and II to employ standard protecting groups in accord with the methods compiled in "Protective Groups in Organic Synthesis" by Theodora W. Greene.

The invention is illustrated further by the following examples, which are not to be construed as limiting the invention in scope or spirit to the specific procedures described in them. Those having skill in the art will recognize that the starting materials may be varied and additional steps employed to produce compounds encompassed by the present inventions, as demonstrated by the following examples. In some cases, protection of reactive functionalities may be necessary to achieve some of the above transformations. In general, such need for protecting groups, as well as the conditions necessary to attach and remove such groups, will be apparent to those skilled in the art of organic synthesis.

EXAMPLES

Example 1

Preparation of 3,4,5,6-tetrahydro-2,3,10-triaza-benzo[e]azulene-1-carboxylic Acid Phenylamide

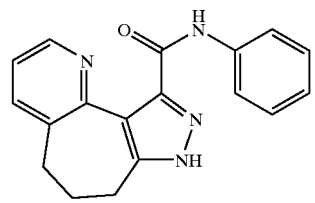

Step 1: 1,3-cycloheptanedione (4.0 g) in 10 mL of dimethylformamide demethyl acetal is stirred at 90° C. for 90 minutes. The excess DMF/DMA is evaporated under vacuum; ether is added to the residue. The mixture is stirred at reflux and cooled. The solid is filtered to give 4.0 g of 2-dimethylaminomethylene-cycloheptane-1,3-dione as a brownish solid. $^1$H NMR (CDCl$_3$): 1.80–1.90(m, 4H), 2.60 (m, 4H), 2.80(s. 3H), 3.30 (s, 3H), 7.70 (s, s, 1H). LR-MS: MW 181.23, Found: 182.1 (M+1).

Step 2: A solution of hydrazine monohydrate (0.7 g) in 5 mL of MeOH is added dropwise to a solution of 2-dimethylaminomethylene-cycloheptane-1,3-dione (2.5 g) in 50 mL of MeOH at 0° C. After addition, the reaction mixture is heated at reflux for 2 hours, then concentrated to a solid in vacuo. The solid is triturated with EtOAc and hexane, and filtered to yield 5,6,7,8-tetrahydro-1H-cycloheptapyrazol-4-one as a tan solid. $^1$H NMR (CDCl$_3$): 1.90–2.10(m, 4H), 2.70(m, 2H), 3.05(t, 2H), 8.05(s, 1H), LR-MS: MW 150.18, Found: 151.2 (M+1).

Step 3: A mixture of 5,6,7,8-tetrahydro-1H-cycloheptapyrazol-4-one (1.5 g), 3-(dimethylamino)-acrolein (Aldrich, 2.0 g, 2 eq.), piperidine (1.7 g, 2 eq.), and NH4OAc (3.0 g, 4 eq.) is heated at 100° C. for 4 hr under N$_2$, then cooled. An additional 2 equivalents of acrolein and NH$_4$OAc are added and the mixture is heated at 100° C. overnight. After cooling, 1 N HCl is added. The reaction mixture it is extracted with CH$_2$Cl$_2$ (4 eq.); the extract is discarded. The aqueous layer is basified with NH$_4$OH and extracted with CH$_2$Cl$_2$ containing 5% EtOH (4 eq.). The combined extracts are washed with water, dried and concentrated to give 3,4,5,6-tetrahydro-2,3,10-triaza-benzo[e] azulene as a glassy oil. $^1$H NMR (CDCl$_3$): 2.05(m, 2H), 2.90(m, 2H), 3.10(t, 2H), 7.00(m, 1H), 7.20(d, 1H), 8.30(s, 1H), 8.40(d, 1H). LR-MS: MW 185.23, Found: 186.06(M+ 1).

Step 4: A mixture of 3,4,5,6-tetrahydro-2,3,10-triaza-benzo[e]azulene (1.0 g), NBS (1.0 g), and sodium acetate (860 mg) in 35 mL of dichloroethane is stirred at 60° C. for 6 hours, and then cooled and diluted with CH$_2$Cl$_2$. The organic mixture is washed with water, dried over Na$_2$SO$_4$, and concentrated to provide 1-bromo-3,4,5,6-tetrahydro-2,3,10-triaza-benzo[e]azulene as a tan solid. $^1$H NMR (CDCl$_3$): 2.10(m, 2H), 2.70 (m, 2H), 2.95 (t, 2H), 7.10 (m, 1H), 7.50 (d, 1H), 8.60 (d, 1H). LR-MS: MW 264.12, Found: 266.0.

Step 5a: 0.6 mL of 1.7 M of t-BuLi in pentane is added dropwise under argon to a stirred solution of 1-bromo-3,4,5,6-tetrahydro-2,3,10-triaza-benzo[e]azulene (100 mg) in 5 mL of anhydrous THF at −78° C. After addition, 55 uL of phenyl isocyanate is added dropwise to the mixture at −78° C. The reaction mixture is allowed to warm to −10° C. over a period of 1 hour, quenched with aqueous NH$_4$Cl solution, and extracted with EtOAc. The extract is washed with water, dried, and concentrated to an oil. Purification on a silica gel plate, eluting with 10% MeOH in CH$_2$Cl$_2$ provides 3,4,5,6-tetrahydro-2,3,10-triaza-benzo[e]azulene-1-carboxylic acid phenylamide as a solid. $^1$H NMR(CDCl$_3$): 2.32(m, 2H), 2.68(t, 2H), 2.87(t, 2H), 7.15(t,1H), 7.27(t,1H), 7.36(t, 2H), 7.68–7.77(m, 3H), 8.61(d, 1H), 13.3(s, 1H). LR-MS: MW 304.35, Found: 305.06(M+1).

Example 2

Preparation of 3,4,5,6-tetrahydro-2,3,10-triaza-benzo[e]azulene-1-carsoxylic Acid [1-(3-azetidin-1-yl-propyl)-1H-pyrazol-3-yl]-amide

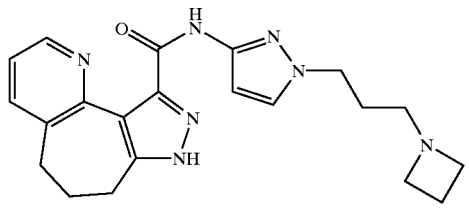

Step 5b: 7.8 mL of 1.7 M of t-BuLi in pentane is added dropwise under argon to a stirred solution of 1-bromo-3,4,5,6-tetrahydro-2,3,10-triaza-benzo[e]azulene (1.4 g) in 75 mL of anhydrous THF at −78° C. After addition, dry carbon dioxide is bubbled into the mixture at the same temperature for 2 hours. The reaction mixture is allowed to warm to room temperature, quenched with 1N HCl solution, and diluted with water. The mixture is basified with 1N NaOH to pH 8–9, and then extracted with EtOAc. The aqueous layer is then acidified with HOAc to pH 4–5 and extracted with CH$_2$Cl$_2$ eight times. The combined extracts are washed with water, dried, and concentrated to give 3,4,5,6-tetrahydro-2,3,10-triaza-benzo[e]azulene-1-carboxylic acid as a tan solid. $^1$H NMR(DMSO): 1.95(m, 2H), 2.96(m, 2H), 3.07(t, 2H), 7.45(m,1H), 7.97(d,1H), 8.52(d, 2H). LR-MS: MW 229.23, Found: 230.2(M+1).

Step 6: A mixture of 3,4,5,6-tetrahydro-2,3,10-triaza-benzo[e]azulene-1-carboxylic acid (80 mg), 1-(3-azetidin-1-yl-propyl)-1H-pyrazol-3-ylamine (68 mg), EDCI(85 mg) and DMAP(55 mg) in 10 mL of 1,2-dichloroethane is refluxed overnight, cooled and diluted with CH$_2$Cl$_2$. The mixture is washed with aqueous NaHCO$_3$ solution, water, dried over Na2SO$_4$ and concentrated under vacuum. Purification on a silica gel plate, eluting with 10% MeOH in CH$_2$Cl$_2$ yields 12 mg of 3,4,5,6-tetrahydro-2,3,10-triaza-benzo[e]azulene-1-carboxylic acid [1-(3-azetidin-1-yl-propyl)-1H-pyrazol-3-yl]-amide as a colorless foam. $^1$H NMR (CDCl$_3$): 2.01–2.31 (m, 6H), 2.67–2.92(m, 8H), 3.63(m, 2H), 4.17(t, 2H), 6.65 (d, 1H), 7.23(m, 1H), 7.33(d, 1H), 7.65(d, 1H), 8.62(d, 1H), 14.13(bs, 1H). LR-MS: MW 391.48, Found: 392.2 (M+1).

Example 3

4-oxo-4,5,6,7-tetrahydro-1H-indazole-3-carboxylic acid[6-(3-diethylamino-propoxy)-pyridin-3-yl]-amide

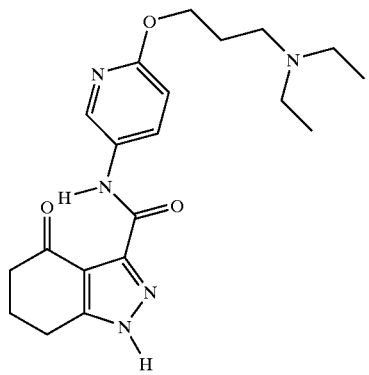

A solution of 2-ethyloxalylcyclohexan-1,3-dione (Synthesis, 1976, 722) (9.50 g, 45 mmol), hydrazine monohydrate (2.2 mL, 45 mmol) and acetic acid (2.6 mL, 45 mmol) in ethanol (100 mL) is stirred at 22° C. for 6 hours. The solvent is evaporated under reduced pressure. The residue is dissolved in acetic acid (100 mL) and stirred under nitrogen at 120° C. for 3 hours. The solvent is evaporated under reduced pressure and the resulting residue is dissolved in chloroform (200 mL), treated with 10% NaCl (100 mL), and neutralized with 1 M sodium carbonate. The organic layer is separated, and the solvent is evaporated to give 4-oxo-4,5,6,7-tetrahydro-1H-indazole-3-carboxylic acid ethyl ester $^1$H NMR (CDCl$_3$) t, J=7.1 Hz, 3H), 2.17 (quintet, J=6.4 Hz, 2H), 2.58 (t, J=6.8 Hz, 2H), 3.00 (t, J=6.2 Hz, 2H), 4.44 (q, J=7.3 Hz, 2H). MW 208.220; MS (M+H)$^+$ 209.

A solution of 4-oxo-4,5,6,7-tetrahydro-1H-indazole-3-carboxylic acid ethyl ester (purity 90%, 1.84 g, 8.0 mmol) in methanol (20 mL) is treated with 10 N NaOH (4 mL) and stirred under nitrogen at 60° C. for 90 min. The solvent is evaporated under reduced pressure and the residue is dissolved in water (30 mL), treated with brine (30 mL) and acidified to pH 2 with conc. hydrochloric acid to produce a white precipitate. The mixture is cooled to 0° C. The precipitate is filtered, washed with water (5 mL), and dried in a vacuum oven to give 4-oxo-4,5,6,7-tetrahydro-1H-indazole-3-carboxylic acid. $^1$H NMR (DMSO-d$_6$) 2.18 (quintet, J=6.2 Hz, 2H), 2.66 (t, J=6.4 Hz, 2H), 2.95 (t, J=6.2 Hz, 2H).

A solution of 4-oxo-4,5,6,7-tetrahydro-1H-indazole-3-carboxylic acid (2.25 g, 12 mmol), 1-(3-dimethylaminopropyl-3-ethylcarbodiimide hydrochloride (2.87 g, 15 mmol), DMAP (1.83 g, 15 mmol), and DMF (10 mL) in dichloromethane (40 mL) is stirred under nitrogen at 20° C. for 2 hours. 6-(3-Diethylamino-propoxy)-pyridin-3-ylamine (2.50 g, 11.2 mmol) is added. The mixture is stirred under nitrogen at 40° C. for 24 hours; and then poured into 10% NaCl, treated with 1 M sodium carbonate to pH 10, and extracted with chloroform (100 mL). The solution is concentrated, diluted with xylenes (100 mL), and the volatiles are thoroughly evaporated under reduced pressure. The residue is purified by column chromatography on silica gel using a mixture of chloroform-methanol-30% ammonium hydroxide (90:9:1, v/v/v) as an eluent and the residue is recrystallized from ethyl acetate to give pure 4-oxo-4,5,6,7-tetrahydro-1H-indazole-3-carboxylic acid [6-(3-diethylamino-propoxy)-pyridin-3-yl]-amide. $^1$H NMR (CD$_3$OD) t, J=7.1 Hz, 6H), 1.97 (m, 2H), 2.25 (quintet, J=6.3 Hz, 2H), 2.62 (q, J=7.1 Hz, 4H), 2.71 (m, 4H), 2.99 (t, J=6.3 Hz, 2H), 4.03 (t, J=6.3 Hz, 2H), 6.81 (dd, J=8.9 and 0.5 Hz, 1H), 8.12 (dd, J=8.9 and 2.7 Hz, 1H), 8.56 (dd, J=2.7 and 0.5 Hz, 1H). MW 385.471; MS (M−H)$^-$ 384.

Example 4

5,7-dihydro-6H-pyrazolo[3,4-H]quinoline-9-carboxylic acid[6-(3-diethylamino-propoxy)-pyridin-3-yl]-amide

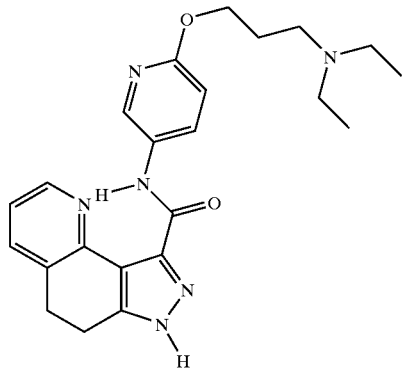

A mixture of 4-oxo-4,5,6,7-tetrahydro-1H-indazole-3-carboxylic acid [6-(3-diethylamino-propoxy)-pyridin-3-yl]-amide (192 mg, 0.50 mmol), 3-(dimethylamino)-acrolein 0.15 mL (1.50 mmol), ammonium acetate (384 mg, 5.00 mmol), and acetic acid (2.0 mL) is stirred under nitrogen at 100° C. for 16 h, poured into ice-cold 10% NaCl (20 mL), treated with 10 N NaOH to pH 12 and extracted with chloroform (30 mL). The extract is concentrated under reduced pressure and the residue is chromatographed on silica gel using chloroform-methanol-30% ammonium hydroxide (90:9:1, v/v/v) as an eluent to give pure 5,7-dihydro-6H-pyrazolo[3,4-h]quinoline-9-carboxylic acid [6-(3-diethylamino-propoxy)-pyridin-3-yl]-amide. $^1$H NMR (CDCl$_3$) t, J=7.1 Hz, 6H), 1.96 (m, 2H), 2.57 (q, J=7.1 Hz, 4H), 2.65 (m, 2H), 3.10 (m, 4H), 4.33 (t, J=6.3 Hz, 2H), 6.80 (d, J=8.8 Hz, 1H), 7.21 (dd, J=7.7 and 4.9 Hz, 1H), 7.66 (d, J=7.7 Hz, 1H), 8.32 (dd, J=8.9 and 2.7 Hz, 1H), 8.44 (d, J=2.7 Hz, 1H), 8.47 (dd, J=4.9 and 1.1 Hz, 1H). MW 420.519; MS (M−H)$^-$ 419.

Example 5

5,7-dihydro-6H-pyrazolo[3,4-H]quinazoline-9-carboxylic acid[6-(3-diethylamino-propoxy)-pyridin-3-yl]-amide

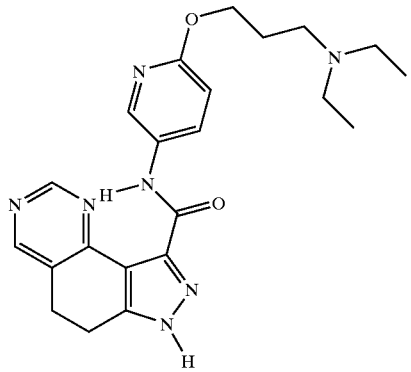

A mixture of 4-oxo-4,5,6,7-tetrahydro-1H-indazole-3-carboxylic acid [6-(3-diethylamino-propoxy)-pyridin-3-yl]-amide (192 mg, 0.50 mmol) and tris(dimethylamino)methane (181 mg, 1.25 mmol) is stirred in a pressure reactor at 60° C. for 5 hours. After cooling, the reaction mixture is dissolved in ethanol (5 mL), treated with formamidine acetate (1.00 g, 9.6 mmol), and stirred in a pressure reactor at 110° C. for 18 hours. The reaction mixture is poured into 10% NaCl (50 mL), treated with 1 M sodium carbonate to pH 11 and extracted with chloroform (40 mL). The extract is dried over sodium carbonate, and the solvent is evaporated under reduced pressure. The residue is triturated with diethyl ether to give pure crystalline 5,7-dihydro-6H-pyrazolo[3,4-h]quinazoline-9-carboxylic acid [6-(3-diethylamino-propoxy)-pyridin-3-yl]-amide. $^1$H NMR (CD$_3$OD) t, J=7.1 Hz, 6H), 1.98 (m, 2H), 2.61 (q, J=7.1 Hz, 4H), 2.69 (m, 2H), 3.10 (m, 2H), 3.16 (m, 2H), 4.32 (t, J=6.2 Hz, 2H), 6.84 (dd, J=8.8 and 0.5 Hz, 1H), 8.17 (dd, J=8.9 and 2.7 Hz, 1H), 8.51 (dd, J=2.7 and 0.5 Hz, 1H), 8.65 (s, 1H), 9.09 (s, 1H) MW 421.507; MS (M+H)$^+$ 422.

Example 6

2-methyl-5,7-dihydro-6H-pyrazolo[3,4-H]quinazoline-9-carboxylic acid[6-(3-diethylamino-propoxy)-pyridin-3-yl]-amide

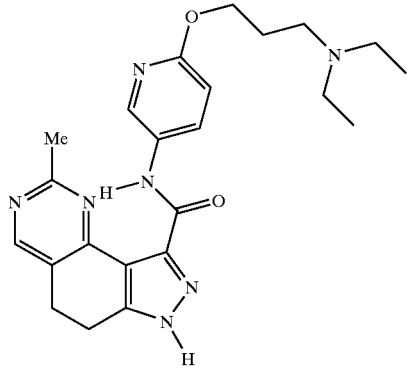

A procedure analogous to that described in Example 6 is used, except that in the second step acetamidine hydrochloride (0.80 g, 8.4 mmol) and sodium acetate (0.68 g, 8.2 mmol) are used instead of formamidine acetate. The crude product is chromatographed on silica gel using chloroform-methanol-30 ammonium hydroxide (95:4.5:0.5, v/v/v) as an eluent. Recrystallization of the separated product from acetone gave pure 2-methyl-5,7-dihydro-6H-pyrazolo[3,4-h]quinazoline-9-carboxylic acid [6-(3-diethylamino-propoxy)-pyridin-3-yl]-amide. $^1$H NMR (DMSO-d$_6$) t, J=7.1 Hz, 6H), 1.80 (quintet, J=6.8 Hz, 2H), 2.43 (q, J=7.1 Hz, 4H), 2.48 (m, 2H), 2.66 (s, 3H), 2.93 (m, 2H), 2.99 (m, 2H), 4.25 (t, J=6.2 Hz, 2H), 6.86 (d, J=8.8 Hz, 1H), 8.06 (dd, m, 1H), 8.45 (m, 1H), 8.61 (s, 1 H). MW 435.534; MS (M–H)$^-$434.

Example 7

2,4,5,6-tetrahydro-1,2,6,7-tetraaza-as-indacene-8-carboxylic acid[6-(3-diethylamino-propoxy)-pyridin-3-yl]-amide

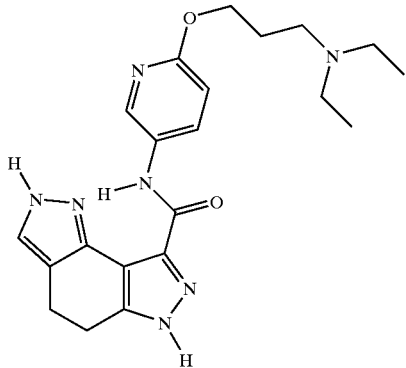

A procedure analogous to that used in Examples 6 and 7 is applied except that, in the second step, hydrazine acetate is used instead of formamidine acetate. The crude product is triturated with diethyl ether to give pure 2,4,5,6-tetrahydro-1,2,6,7-tetraaza-as-indacene-8-carboxylic acid [6-(3-diethylamino-propoxy)-pyridin-3-yl]-amide. $^1$H NMR (CD$_3$OD) t, J=7.1 Hz, 6H), 1.97 (m, 2H), 2.61 (q, J=7.1 Hz, 4H), 2.68 (m, 2H), 2.98 (m, 2H), 4.29 (t, J=6.2 Hz, 2H), 6.81 (dd, J=8.8 and 0.5 Hz, 1H), 7.47 (s, 1H), 8.20 (m, 1H), 8.53 (s, 1 H). MW 409.496; MS (M–H)$^-$ 408.

Example 8

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}$C), hydrogen (preferably $^3$H), sulfur (preferably $^{35}$S), or iodine (preferably $^{125}$I). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kan.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph. In addition, tritium may also be introduced by tritium-halogen exchange with tritium gas, transition metal catalyzed tritium gas reduction of unsaturated bonds, or sodium borotritide reduction of ketones, aldehydes, and imines.

Example 9

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

Example 10

Binding Assay

This assay is a standard assay for GABA$_A$ binding affinity. The high affinity and high selectivity of compounds of this invention for the benzodiazepine site of the GABA$_A$ receptor is confirmed using the binding assay described in Thomas and Tallman (J. Bio. Chem. 1981; 156:9838–9842, and J. Neurosci. 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted and the pellet stored at –20° C. overnight. The pellet is then thawed, resuspended in 25 volumes of Buffer A (original wt/vol), centrifuged at 20,000×g and the supernatant is then decanted. This wash step is repeated once. The pellet is finally resuspended in 50 volumes of Buffer A.

Incubations containing 100 μl of tissue homogenate, 100 μl of radioligand, (0.5 nM $^3$H-Ro15-1788 [$^3$H-Flumazenil], specific activity 80 Ci/mmol), and test compound or control (see below), and are brought to a total volume of 500 μl with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^3$H Ro15-1788 with 10 μM Diazepam (Research Biochemicals International, Natick, Mass.). Data were collected in triplicate, averaged, and percent inhibition of total specific binding (Total Specific Binding=Total–Nonspecific) is calculated for each compound.

A competition binding curve is obtained with up to 11 points spanning the compound concentration range from $10^{-12}$ M to $10^{-5}$M obtained per curve by the method described above for determining percent inhibition. K$_i$ values are calculated according the Cheng-Prussof equation.

When tested using this assay, preferred compounds of Formula I exhibit $K_i$ values of less than 1 uM, more preferred compounds of the invention have $K_i$ values of less than 500 nM, and particularly preferred compounds have $K_i$ values of less than 100 nM. Compounds 11–32 exhibit $K_i$ values of less than 1 uM.

Example 11

Electrophysiology

The following assay is used to determine if a compound of the invention act as an agonist, an antagonist, or an inverse agonist at the benzodiazepine site of the $GABA_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. *Xenopus Laevis* oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. NM 021911; human $\beta_3$, GENBANK accession no. M82919 and accession no. Z20136; human $\gamma_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\beta_2$, GENBANK accession no. L08497. For each subunit combination, sufficient message for each constituent subunit is injected to provide current amplitudes of >10 nA when 1 μM GABA is applied.

Compounds are evaluated against a GABA concentration that evokes <10% of the maximal evokable GABA current (e.g. 1 μM–9 μM). Each oocyte is exposed to increasing concentrations of compound in order to evaluate a concentration/effect relationship. Compound efficacy is calculated as a percent-change in current amplitude: 100*((Ic/I)−1), where Ic is the GABA evoked current amplitude observed in the presence of test compound and I is the GABA evoked current amplitude observed in the absence of the test compound.

Specificity of a compound for the benzodiazepine site is determined following completion of a concentration/effect curve. After washing the oocyte sufficiently to remove previously applied compound, the oocyte is exposed to GABA+1 μM RO15-1788, followed by exposure to GABA+1 μM RO15-1788+test compound. Percent change due to addition of compound is calculated as described above. Any percent change observed in the presence of RO15-1788 is subtracted from the percent changes in current amplitude observed in the absence of 1 μM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula

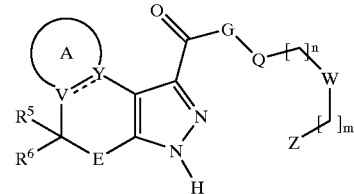

or a pharmaceutically acceptable salt thereof, wherein:

E represents $(CR^1R^2)_k$ wherein $R^1$ and $R^2$ are independently chosen from hydrogen, halogen, hydroxy, cyano, nitro, amino, alkyl, alkenyl, alkynyl, haloalkyl, haloalkoxy, mono- and di-alkylamino, and alkoxy;

k is 0, 1, 2, or 3;

G is either oxygen or NH;

the group

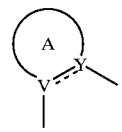

represents a pyrido ring optionally substituted with 1, 2, or 3 groups that are independently $R^3$, $R^{3'}$, or $R^4$;

V is carbon;

Y is carbon;

$R^3$, $R^{3'}$ and $R^4$ are independently chosen at each occurrence, and carry the same definitions as $R^5$ and $R^6$;

$R^5$ and $R^6$ may be taken together to form a carbonyl group; or $R^5$ and $R^6$ are independently chosen from hydrogen, halogen, hydroxy, haloalkyl, haloalkoxy, nitro, cyano, —COOH, amino, $R_{10}$, —NH($R_{10}$), —N($R_{10}$)($R_{11}$), —O($R_{10}$), —SO$_2$NH$_2$, —SO$_2$NH($R_{10}$), —SO$_2$N($R_{10}$)($R_{11}$), —NHCO($R_{10}$), —N($R_{10}$)CO($R_{11}$), —NHCO$_2$($R_{10}$), —N($R_{10}$)CO$_2$($R_{11}$), —NHSO$_2$($R_{10}$), —N($R_{10}$)SO$_2$($R_{11}$), —SO$_2$NHCO($R_{10}$), —SO$_2$N($R_{10}$)CO($R_{11}$), —CONHSO$_2$($R_{10}$), —CON($R_{10}$)SO$_2$($R_{11}$), —CONH$_2$, —CONH($R_{10}$), —CON($R_{10}$)($R_{11}$), —CO$_2$($R_{10}$), —CO($R_{10}$), —SO$_{0-2}$($R_{10}$), optionally substituted aryl, where the aryl group is optionally substituted at one or more substitutable positions with $C_1$–$C_6$ alkyl, $C_1$–$C_6$ alkoxy, halogen, hydroxy, cyano, nitro, amino, mono- or di-($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino ($C_1$–$C_6$)alkyl, mono- or di ($C_1$–$C_6$)alkylamino ($C_1$–$C_6$)alkyl and optionally substituted heteroaryl, wherein the heteroaryl group is optionally substituted with halogen, cyano, hydroxyl, nitro, azido, amino, oxo, alkanoyl, carboxamido, alkylcarboxamido, $C_1$–$C_8$ alkyl, $C_2$–$C_8$ alkenyl, $C_2$–$C_8$ alkynyl, $C_1$–$C_8$ alkoxy, phenoxy, $C_1$–$C_8$ alkylthio, $C_1$–$C_8$ alkylsulfinyl, $C_1$–$C_8$ alkylsulfonyl, amino($C_1$–$C_8$)alkyl, mono- and di-($C_1$–$C_8$)alkylamino, haloalkyl, haloalkoxy, alkanoyloxy, alkoxycarbonyl, carbocyclic groups selected from phenyl and naphthyl, cycloalkyl, cyclopropylmethyl, cyclohexenyl, arylalkyl cycloalkylalkyl, arylalkoxy having 1 to 3 separate or fused rings and from 6 to about 18 carbon ring atoms, heterocyclic groups selected from partially unsaturated, heteroaromatic, and heteroalicyclic groups selected from coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl; heterocyclicalkyl groups, heteroarylalkyl groups, and heteroalicyclic alkyl groups;

$R_{10}$ and $R_{11}$ are independently chosen from straight, branched, and cyclic alkyl groups and (cycloalkyl)alkyl groups, said straight, branched, and cyclic alkyl groups and (cycloalkyl)alkyl groups consisting of 1 to 8 carbon atoms, and containing zero or one or more double or triple bonds, each of which 1 to 8 carbon atoms may be further substituted with one or more substituent(s) independently chosen from hydroxy, oxo, halogen, amino, mono or dialkylamino, cyano, nitro, alkoxy, —COOH, —SO$_2$NH$_2$, —SO$_2$NH(alkyl), —SO$_2$N(alkyl)(alkyl), —NHCO(alkyl), —N(alkyl)CO(alkyl), —NHCO$_2$(alkyl), —N(alkyl)CO$_2$(alkyl), —NHSO$_2$(alkyl), —N(alkyl)SO$_2$(alkyl), —SO$_2$N(alkyl)CO(alkyl), —SO$_2$NHCO(alkyl), —CON(alkyl)SO$_2$(alkyl), —CONHSO$_2$(alkyl), —CONH$_2$, —CONH(alkyl), —CON(alkyl)(alkyl), —CO$_2$(alkyl), —CO(alkyl), —SO$_{0-2}$(alkyl), cycloalkyl, aryl, heteroaryl, and heterocycloalkyl;

Q is an optionally substituted aryl, where the aryl group is substituted in one or more substitutable positions with $C_1$–$C_6$ alkyl, $C_1$–$C_6$ alkoxy, halogen, hydroxy, cyano, nitro, amino, mono- or di-($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono- or di ($C_1$–$C_6$) alkylamino ($C_1$–$C_6$)alkyl or optionally substituted heteroaryl group, wherein the heteroaryl group is unsubstituted or substituted with up to three substituents independently selected from i) and ii) wherein
i) represents hydroxy, cyano, halogen, nitro, amino, mono- or di-($C_1$–$C_6$)alkylamino, ($C_2$–$C_6$)alkenyl, ($C_2$–$C_6$)alkynyl, ($C_1$–$C_6$)alkoxy, trifluoromethyl, or trifluoromethoxy;
ii) represents straight or branched chain ($C_1$–$C_6$)alkyl optionally containing heteroatoms and optionally substituted with one or more carbocyclic or heterocyclic group;

W is hydrogen, oxygen, NR$^7$, sulfur, or CR$^7$R$^8$ where R$^7$ and R$^8$ are the same or different and represent hydrogen, straight or branched chain alkyl, or CR$^7$R$^8$ represents a cycloalkyl group having from 3 to 7 carbon atoms;

Z is absent, hydrogen, hydroxy, straight or branched chain alkoxy, cycloalkyl, cycloalkyl(alkoxy), amino, mono- or di-alkylamino, or NR$_{12}$COR$_{13}$, where R$_{12}$ and R$_{13}$ are the same or different and represent hydrogen or straight or branched chain alkyl, or R$_{12}$ and R$_{13}$ may be joined to form a heterocycloalkyl ring, or Z is an optionally substituted carbocyclic or an optionally substituted heterocyclic group, wherein each of the above is optionally substituted with one or more groups that are independently halogen, cyano, hydroxyl, nitro, azido, amino, oxo, alkanoyl, carboxamido, alkylcarboxamido, $C_1$–$C_8$ alkyl, $C_2$–$C_8$ alkenyl, $C_2$–$C_8$ alkynyl, $C_1$–$C_8$ alkoxy, phenoxy, $C_1$–$C_8$ alkylthio, $C_1$–$C_8$ alkylsulfinyl, $C_1$–$C_8$ alkylsulfonyl, amino ($C_1$–$C_8$)alkyl, mono- and di-($C_1$–$C_8$)alkylamino, haloalkyl, haloalkoxy, alkanoyloxy, alkoxycarbonyl, carbocyclic groups selected from phenyl and naphthyl, cycloalkyl, cyclopropylmethyl, cyclohexenyl, arylalkyl cycloalkylalkyl, arylalkoxy having 1 to 3 separate or fused rings and from 6 to about 18 carbon ring atoms, heterocyclic groups selected from partially unsaturated, heteroaromatic, and heteroalicyclic groups selected from coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl; heterocyclicalkyl groups, heteroarylalkyl groups, and heteroalicyclic groups;

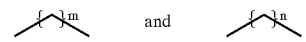

represent methylene groups which may be substituted with halogen, cyano, nitro, amino, mono- or di-alkylamino, alkenyl, alkynyl, alkoxy, trifluoromethyl, trifluoromethoxy, straight or branched chain alkyl or cycloalkyl;

m is 0, 1, 2, or 3; and n is 0, 1, 2, or 3;

with the proviso that when W is hydrogen, m is 0 and Z is absent.

2. A compound according to claim 1 of the formula

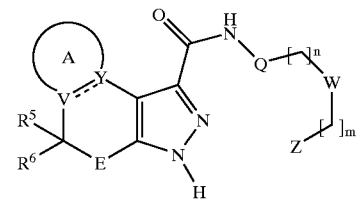

or a pharmaceutically acceptable salt thereof, wherein:

E represents (CR$^1$R$^2$)$_k$, wherein R$^1$ and R$^2$ are independently chosen from hydrogen, halogen, hydroxy, cyano, nitro, amino, ($C_1$–$C_6$)alkyl, ($C_2$–$C_6$)alkenyl, ($C_2$–$C_6$)alkynyl, halo($C^1$–$C_6$)alkyl, halo($C_1$–$C_6$)alkoxy, mono- and di-alkyl($C_1$–$C_6$)amino, and ($C_1$–$C_6$)alkoxy;

k is 0, 1, 2, or 3;

the group

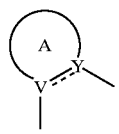

is a group of the formula:

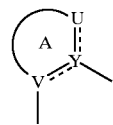

which represents a pyrido ring optionally substituted at any available carbon by $R^3$, $R^{3'}$, and $R^4$;

wherein the $U\!=\!\!=\!Y$ and $V\!=\!\!=\!Y$ bonds are aromatic;

U is nitrogen;

V is carbon;

Y is carbon;

$R^4$ is chosen from hydrogen, $(C_1$–$C_6)$alkyl, optionally substituted aryl, where the aryl group is optionally substituted at one or more substitutable positions with $C_1$–$C_6$ alkyl, $C_1$–$C_6$ alkoxy, halogen, hydroxy, cyano, nitro, amino, mono- or di-$(C_1$–$C_6)$alkylamino, $C_2$–$C_6$alkenyl, $C_2$–$C_6$alkynyl, $C_1$–$C_6$ haloalkyl, $C_1$–$C_6$ haloalkoxy, amino$(C_1$–$C_6)$alkyl, mono- or di$(C_1$–$C_6)$alkylamino$(C_1$–$C_6)$alkyl and heteroaryl groups, said heteroaryl groups having from 1 to 3 rings, 5 to 7 ring members in each ring and, in at least one of said rings, from 1 to about 3 heteroatom selected from N, O, and S;

$R^3$, $R^{3'}$, and $R^4$ are independently chosen at each occurrence, and carry the same definitions as $R^5$ and $R^6$;

$R^5$ and $R^6$ may be taken together to form a carbonyl group; or $R^5$ and $R^6$ are independently chosen from hydrogen, halogen, hydroxy, haloalkyl, haloalkoxy, nitro, cyano, —COOH, amino, $R_{10}$, —NH($R_{10}$), —N($R_{10}$)($R_{11}$), —O($R_{10}$), —SO$_2$NH$_2$, —SO$_2$NH($R_{10}$), —SO$_2$N($R_{10}$)($R_{11}$), —NHCO($R_{10}$), —N($R_{10}$)CO($R_{11}$), —NHCO$_2$($R_{10}$), —N($R_{10}$)CO$_2$($R_{11}$), —NHSO$_2$($R_{10}$), —N($R_{10}$)SO$_2$($R_{11}$), —SO$_2$NHCO($R_{10}$), —SO$_2$N($R_{10}$)CO($R_{11}$), —CONHSO$_2$($R_{10}$), —CON($R_{10}$)SO$_2$($R_{11}$), —CONH$_2$, —CONH($R_{10}$), —CON($R_{10}$)(R11), —CO$_2$($R_{10}$), —CO($R_{10}$), —SO$_{0\text{-}2}$($R_{10}$), optionally substituted aryl groups, and heteroaryl groups;

$R_{10}$ and $R_{11}$ are independently chosen from straight, branched, and cyclic alkyl groups and (cycloalkyl)alkyl groups, said straight, branched, and cyclic alkyl groups and (cycloalkyl)alkyl groups consisting of 1 to 8 carbon atoms, and containing zero or one or more double or triple bonds, each of which 1 to 8 carbon atoms may be further substituted with one or more substituent(s) independently chosen from hydroxy, oxo, halogen, amino, mono or dialkylamino, cyano, nitro, alkoxy, —COOH, —SO$_2$NH$_2$, —SO$_2$NH($C_1$-$C_4$alkyl), —SO$_2$N($C_1$-$C_4$alkyl)($C_1$-$C_4$alkyl), —NHCO($C_1$-$C_4$alkyl), —N($C_1$-$C_4$alkyl)CO($C_1$-$C_4$alkyl), —NHCO$_2$($C_1$-$C_4$alkyl), —N($C_1$-$C_4$alkyl)CO$_2$($C_1$-$C_4$alkyl), —NHSO$_2$($C_1$-$C_4$alkyl), —N($C_1$-$C_4$alkyl)SO$_2$($C_1$-$C_4$alkyl), —SO$_2$N($C_1$-$C_4$alkyl)CO($C_1$-$C_4$alkyl), —SO$_2$NHCO($C_1$-$C_4$alkyl), —CON($C_1$-$C_4$alkyl)SO$_2$($C_1$-$C_4$alkyl), —CONHSO$_2$($C_1$-$C_4$alkyl), —CONH$_2$, —CONH($C_1$-$C_4$alkyl), —CON($C_1$-$C_4$alkyl)($C_1$-$C_4$alkyl), —CO$_2$($C_1$-$C_4$alkyl), —CO($C_1$-$C_4$alkyl), —SO$_{0\text{-}2}$($C_1$-$C_4$alkyl), $C_3$–$C_7$cycloalkyl, phenyl, pyridyl, pyrimidinyl, pyrazolyl, pyrrolyl, imidazolyl, thienyl, azetidinyl, pyrrolidinyl piperidinyl, piperazinyl, and morpholinyl groups;

Q represents a phenyl, naphthyl, quinolinyl, thienyl, pyridyl, pyrimidinyl, pyrazinyl, oxazolyl, isoxazolyl, symmetrical or unsymmetrical oxadiazolyl, symmetrical or unsymmetrical thiadiazolyl, symmetrical or unsymmetrical triazolyl, pyrrolyl, imidazolyl, pyrazolyl, furanyl, diazenyl, triazenyl, or triazolopyrazinyl group, each of which may be unsubstituted or substituted with up to three substituents independently selected from i) and ii) wherein i) represents hydroxy, cyano, halogen, nitro, amino, mono- or di-$(C_1$–$C_6)$alkylamino, $(C_2$–$C_6)$alkenyl, $(C_2$–$C_6)$alkynyl, $(C_1$–$C_6)$alkoxy, trifluoromethyl, or trifluoromethoxy;

ii) represents straight or branched chain $(C_1$–$C_6)$alkyl optionally containing heteroatoms and optionally substituted with one or more carbocyclic or heterocyclic group;

W is hydrogen, oxygen, NR$^7$, sulfur, or CR$^7$R$^8$ where R$^7$ and R$^8$ are the same or different and represent hydrogen, straight or branched chain $(C_1$–$C_6)$alkyl, or CR$^7$R$^8$ represent a $C_3$–$C_7$ cycloalkyl group;

Z is absent, hydrogen, hydroxy, straight or branched chain $(C_1$–$C_6)$alkoxy, $(C_3$–$C_7)$cycloalkyl, $(C_3$–$C_7)$cycloalkyl$(C_1$–$C_3)$alkoxy, amino, mono or di$(C_1$–$C_6)$alkylamino, a non-aromatic carbocyclic, a non-aromatic heterocyclic group, or NR$_{12}$COR$_{13}$, where R$_{12}$ and R$_{13}$ are the same or different and represent hydrogen or straight or branched chain $(C_1$–$C_6)$alkyl, or R$_{12}$ and R$_{13}$ may be joined to form a 3 to 8 membered heterocycloalkyl ring, or Z is a phenyl, napthyl, quinolinyl, thienyl, thiazolyl, pyridyl, pyrimidinyl, imidazolyl, pyrazolyl, pyrazinyl, pyridizinyl, piperidinyl, oxazolyl, isoxazolyl, symmetrical or unsymmetrical thiadiazolyl, symmetrical or unsymmetrical triazolyl, symmetrical or unsymmetrical oxadiazolyl, pyrrolyl, furanyl, pyrimidinyl, diazenyl, triazenyl, 1,2,4-triazolone, 4,5-dihydroimidazolyl, or 1,4,5,6-tetrahydropyrimidinyl group;

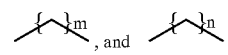, and represent methylene groups which may be unsubstituted or substituted with halogen, cyano, nitro, amino, mono- or di-$(C_1$–$C_6)$alkylamino, $(C_2$–$C_6)$alkenyl, $(C_2$–$C_6)$alkynyl, $(C_1$–$C_6)$alkoxy, trifluoromethyl, trifluoromethoxy, straight or branched chain $(C_1$–$C_6)$alkyl, or $(C_3$–$C_7)$cycloalkyl;

m is 0, 1, 2, or 3; and n is 0, 1, 2, or 3;

with the proviso that when W is hydrogen, m is 0 and Z is absent.

3. A compound or salt according to claim 2 wherein $R^3$, $R^{3'}$, $R^4$, $R^5$, and $R^6$ are independently chosen from hydrogen, halogen, hydroxy, nitro, cyano, amino, —COOH, (C₁–C₄)alkyl, halo(C₁–C₂)alkyl, halo (C₁–C₂)alkoxy, mono- and di-(C₁–C₄)alkylamino, and C₁–C₄alkoxy.

4. A compound or salt according to claim 2, of the formula:

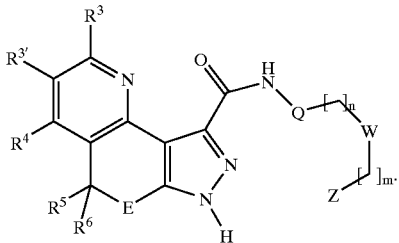

5. A compound or salt according to claim 4, where E represents (CR¹R²)₂ and R¹ and R² are independently hydrogen or methyl.

6. A compound or salt according to claim 5 where R¹ and R² are hydrogen.

7. A compound or salt according to claim 5, wherein R³, R³', R⁴, R⁵, and R⁶, are independently chosen from hydrogen, halogen, amino, hydroxy, methyl, ethyl, methoxy, and ethoxy.

8. A compound or salt according to claim 4, wherein R³, R³', R⁴, R⁵, and R⁶, are hydrogen.

9. A compound or salt according to claim 6, wherein Q is chosen from phenyl, pyridyl, pyrimidinyl, thienyl, pyrrolyl, pyrazolyl, and imidazolyl.

10. A compound or salt according to claim 9, wherein W is oxygen, NH, or CH₂.

11. A compound or salt according to claim 9, wherein Z is hydrogen, hydroxy, straight or branched chain (C₁–C₆)alkoxy, (C₃–C₇)cycloalkyl, (C₃–C₇)cycloalkyl (C¹–C₃)alkoxy, amino, mono or di-(C₁–C₆)alkylamino, C₃–C₇cycloalkyl, azetidinyl, pyrrolidinyl, morpholinyl, piperazinyl, or piperidinyl, or NR₁₂COR₁₃, where R₁₂ and R₁₃ are the same or different and represent hydrogen or straight or branched chain (C₁–C₆)alkyl, or R₁₂ and R₁₃ may be joined to form a 3 to 8 membered heterocycloalkyl ring, or Z is a phenyl, thienyl, thiazolyl, pyridyl, pyrimidinyl, imidazolyl, pyrazolyl, pyridizinyl, oxazolyl, isoxazolyl, symmetrical or unsymmetrical thiadiazolyl, symmetrical or unsymmetrical triazolyl, symmetrical or unsymmetrical oxadiazolyl, pyrrolyl, furanyl, pyrimidinyl, diazenyl, or triazinyl group.

12. A compound or salt according to claim 9, wherein Z is hydrogen, hydroxy, straight or branched chain (C₁–C₆)alkoxy, (C₃–C₇)cycloalkyl, (C₃–C₇)cycloalkyl (C¹–C₃)alkoxy, amino, mono or di-(C₁–C₆)alkylamino, C₃–C₇cycloalkyl, azetidinyl, pyrrolidinyl, morpholinyl, piperazinyl, or piperidinyl.

13. A compound or salt according to claim 4, where E represents CR¹R² and R¹ and R² are independently hydrogen or methyl.

14. A compound or salt according to claim 13, wherein
R¹ and R² are hydrogen; and
R³, R³', and R⁴ are independently chosen from hydrogen, halogen, amino, hydroxy, methyl, ethyl, methoxy, and ethoxy.

15. A compound according to claim 1 which is 3,4,5,6-Tetrahydro-2,3,10-triaza-benzo[e]azulene-1-carboxylic acid phenylamide, or a pharmaceutically acceptable salt thereof.

16. A compound according to claim 1 which is 3,4,5,6-Tetrahydro-2,3,10-triaza-benzo[e]azulene-1-carboxylic acid [1-(3-azetidin-1-yl-propyl)-1H-pyrazol-3-yl]-amide, or a pharmaceutically acceptable salt thereof.

17. A compound according to claim 1 which is 5,7-Dihydro-6H-pyrazolo[3,4-h]quinoline-9-carboxylic acid [6-(3-diethylamino-propoxy)-pyridin-3-yl]-amide, or a pharmaceutically acceptable salt thereof.

18. A pharmaceutical composition comprising a compound or salt according to claim 1, in combination with at least one pharmaceutically acceptable carrier or excipient.

19. The pharmaceutical composition of claim 18, wherein the pharmaceutical composition is formulated as an injectable fluid, an aerosol, a cream, a gel, a pill, a capsule, a syrup, or a transdermal patch.

* * * * *